US008815212B2

(12) United States Patent
Emelianov et al.

(10) Patent No.: US 8,815,212 B2
(45) Date of Patent: Aug. 26, 2014

(54) NANOCARRIERS FOR IMAGING AND THERAPY APPLICATIONS

(75) Inventors: Stanislav Emelianov, Austin, TX (US); Katheryne Wilson, Chehalis, WA (US); Kimberly Homan, Austin, TX (US)

(73) Assignee: Board of Regents, The University of Texas System, Austin, TX (US)

(*) Notice: Subject to any disclaimer, the term of this patent is extended or adjusted under 35 U.S.C. 154(b) by 30 days.

(21) Appl. No.: 13/426,243

(22) Filed: Mar. 21, 2012

(65) Prior Publication Data

US 2012/0197114 A1    Aug. 2, 2012

Related U.S. Application Data

(63) Continuation-in-part of application No. PCT/US2010/049572, filed on Sep. 21, 2010.

(60) Provisional application No. 61/244,088, filed on Sep. 21, 2009.

(51) Int. Cl.
| *A61B 5/055* | (2006.01) |
| *A61B 8/00* | (2006.01) |
| *A61K 9/51* | (2006.01) |
| *A61K 9/00* | (2006.01) |
| *A61K 49/22* | (2006.01) |
| *A61K 47/24* | (2006.01) |
| *A61K 49/00* | (2006.01) |
| *A61K 47/06* | (2006.01) |
| *A61K 47/42* | (2006.01) |
| *A61K 47/30* | (2006.01) |

(52) U.S. Cl.
CPC ............... *A61K 47/24* (2013.01); *A61K 9/5115* (2013.01); *A61K 9/0004* (2013.01); *A61K 49/226* (2013.01); *A61K 9/0009* (2013.01); *A61K 49/00* (2013.01); *A61K 47/06* (2013.01); *A61K 47/42* (2013.01); *A61K 47/30* (2013.01); *A61K 9/5169* (2013.01)
USPC ............................... 424/9.3; 424/9.4; 424/9.5

(58) Field of Classification Search
USPC ............ 424/400–407, 489–498, 9.3, 9.4, 9.5; 600/407–480
See application file for complete search history.

(56) References Cited

U.S. PATENT DOCUMENTS

| 2004/0222413 | A1 | 11/2004 | Hsu et al. | |
| 2005/0208328 | A1 | 9/2005 | Hsu et al. | |
| 2005/0209388 | A1 | 9/2005 | Hsu et al. | |
| 2011/0020242 | A1* | 1/2011 | Zheng et al. | 424/9.34 |
| 2011/0038941 | A1* | 2/2011 | Lee et al. | 424/498 |
| 2011/0104056 | A1* | 5/2011 | Hara et al. | 424/1.65 |
| 2012/0082728 | A1* | 4/2012 | Schneider et al. | 424/491 |
| 2012/0100218 | A1* | 4/2012 | Forrest et al. | 424/489 |
| 2012/0156499 | A1* | 6/2012 | Torchilin et al. | 428/407 |
| 2013/0115254 | A1* | 5/2013 | Odom et al. | 424/400 |

OTHER PUBLICATIONS

International Search Report for International Application No. PCT/US2010/049572 Mailing Date Jun. 16, 2011, 4 pages.

(Continued)

*Primary Examiner* — Sanjay Cattungal
(74) *Attorney, Agent, or Firm* — Baker Botts L.L.P.

(57) ABSTRACT

Nanocarriers and methods of preparation and use of nanocarriers are presented. In some embodiments, a nanocarrier composition comprises an organic liquid comprising a plurality of nanoparticles dispersed therein; and a coating material disposed around the exterior surface of the organic liquid. Biological tissue may be imaged or treated by coming into contact with a nanocarrier composition, and, at least in some embodiments, irradiated.

13 Claims, 15 Drawing Sheets

(56) References Cited

OTHER PUBLICATIONS

Written Opinion of the International Searching Authority for International Application No. PCT/US2010/049572 Mailing Date Jun. 16, 2011, 5 pages.

"Development of a new technology for the production of microcapsules based in atomization processes" by E.P. Herrero et al., Chemical Engineering Journal 117 (2006) 137-142.

"Rebinding and recognition properties of protein-macromolecularly imprinted calcium phosphate/alginate hydrid polymer microspheres" by Kongyin Zhao et al., Reactive & Functional Polymers 60 (2008) 732-741.

"Biomedical photoacoustics beyond thermal expansion u sing triggered nanodroplet vaporization for contrast-enhanced imaging" by Katheryne Wilson et al., Nature Communications 3:618, 10 pages.

* cited by examiner

Original Microscopy Image

Binary Image

Nanocarriers Outlined, Counted and Sized

NANOCARRIERS FOR IMAGING AND THERAPY APPLICATIONS

CROSS REFERENCE TO RELATED APPLICATIONS

This application is a continuation in part of PCT/US10/49572, filed Sep. 21, 2010 and claims priority to U.S. Provisional Application No. 61/244,088, filed Sep. 21, 2009, both of which are incorporated herein by reference.

BACKGROUND

There is a need for reliable, non-invasive tools to detect, diagnose, characterize, and treat diseased tissues, such as cancer—one of the leading causes of death in the United States. The early detection of disease is necessary for effective therapeutic outcome and is a primary indicator for long term survival. For example, detecting the size and proper boundaries of tumor regions are critical diagnostic problems in medicine. Moreover, demarcating tumor boundaries with high specificity is required to direct therapeutic interventions to tumor location and cause less or no damage to the surrounding healthy tissue. Imaging tools that can also provide therapeutic applications can insure quick treatment and provide for the best healing opportunities.

Current imaging modalities suffer from many drawbacks. Optical imaging, for example, suffers from a shallow penetration depth on the order of millimeters. Additionally, ionizing imaging modalities, such as X-ray, computed tomography, and positron emission tomography, present safety concerns. Furthermore, current technologies employed in cancer treatments cause surrounding healthy tissue damage along with tumor necrosis, and such treatments require separate applications and multiple visits.

Biological processes that lead to disease may occur at the molecular level. Nanotechnology offers unprecedented access to the machinery of living cells, and therefore provides the opportunity to study and interact with normal and cancerous cells in real time, at the molecular and cellular scales, and during the earliest stages of the cancer process. Studies have shown gold nanoparticles can be functionalized with antibodies to specifically bind to molecular markers that are indicative of highly proliferative cells. Furthermore, antibodies can target receptors that are overexpressed on the surface of different types of cancerous cells.

Photoacoustic imaging is a technique that can provide functional information based on differences in optical absorption properties of the tissue constituents. The absorption of electromagnetic energy, such as light, and the subsequent emission of an acoustic wave by the tissue is the premise of photoacoustic imaging. Specifically for photoacoustic imaging, the tissue is irradiated with nanosecond pulses of low energy laser light. Broadband ultrasonic acoustic waves may be generated within the irradiated volume; the tissue absorbs the light and then undergoes rapid thermoelastic expansion. An ultrasound transducer and associated receiver electronics may be used to acquire the photoacoustic signal.

Photoacoustic signal can be generated through four mechanisms including thermal (also referred as thermoelastic) expansion, vaporization, photochemical processes, and optical breakdown. However, in biomedical applications of photoacoustic imaging and sensing, the only biologically safe mechanism to date is thermal expansion. Unfortunately, thermal expansion is one of the least efficient mechanisms of light-sound energy conversion and produces acoustic waves of relatively low amplitude. In thermal expansion-based photoacoustic imaging, sufficiently short laser pulses are absorbed by tissue chromophores, causing localized volume heating, leading to rapid expansion and generation of acoustic pressure waves. With the exception of melanin, hemoglobin, and other porphyrins, tissue components have relatively low optical absorption properties, limiting the overall endogenous contrast in photoacoustic imaging.

Current technologies for ultrasound and photoacoustic imaging utilize contrast agents, such as acoustic droplets and metal nanoparticles, respectively. The metal nanoparticles typically range between about 1-about 100 nanometers, while the ultrasound contrast agents have diameters on the order of micrometers. Consequently, current ultrasound contrast agents are too large and/or bulky to be useful in passive diffusion into tumor tissues, for cellular imaging, or to pass through small capillaries and reach certain diseased sites.

SUMMARY

The present disclosure generally relates to nanocarrier compositions and methods of imaging and therapy. More particularly, the present disclosure relates to nanocarrier compositions and methods for selectively imaging and providing therapy to biological tissue.

In one embodiment, the present disclosure provides a nanocarrier comprising: an organic liquid comprising a plurality of nanoparticles dispersed therein; and a coating material disposed around the exterior surface of the organic liquid.

In another embodiment, the present disclosure provides a method of imaging comprising: providing a nanocarrier composition comprising an organic liquid comprising a plurality of nanoparticles dispersed therein, and a coating material disposed around the exterior surface of the organic liquid; and imaging a biological tissue comprising the nanocarrier composition.

In yet another embodiment, the present disclosure provides a method of therapy comprising: contacting a biological tissue with a nanocarrier composition comprising an organic liquid comprising a plurality of nanoparticles dispersed therein, a coating material disposed around the exterior surface of the organic liquid, and a therapeutic agent.

The features and advantages of the present invention will be apparent to those skilled in the art. While numerous changes may be made by those skilled in the art, such changes are within the spirit of the invention.

DRAWINGS

Some specific example embodiments of the disclosure may be understood by referring, in part, to the following description and the accompanying drawings.

Figure 9:
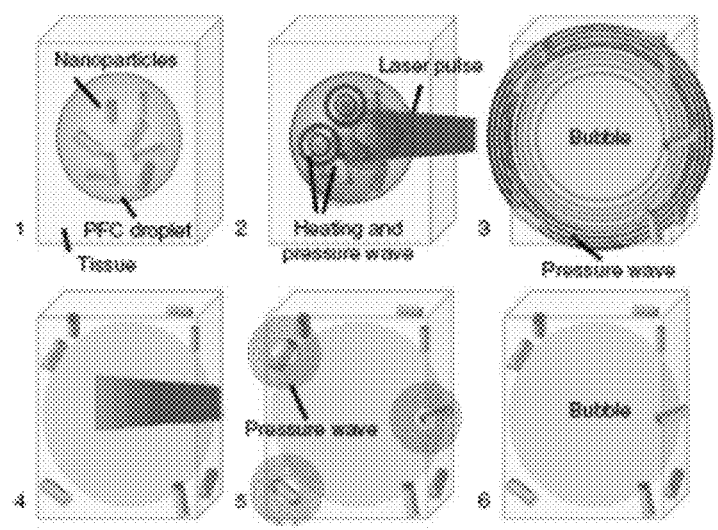

FIG. 9 illustrates a step-by-step diagram of remote activation of PAnDs, providing photoacoustic signal via two mechanisms: vaporization of PAnDs (steps 2-3) and thermal expansion caused by plasmonic nanoparticles (steps 4-5). The resulting gas microbubble of PFC (step 6) provides ultrasound contrast due to acoustic impedance mismatch between gas and the surround environment.

Figure 10:
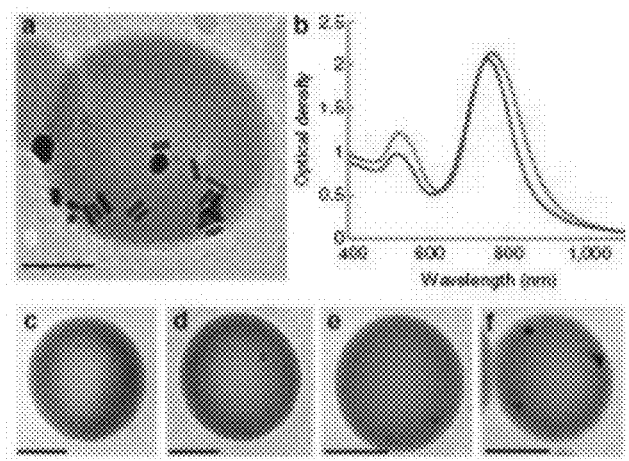

FIG. 10 illustrates Photoacoustic nanoDroplets (PAnDs). (a) Cryogenic transmission electron microscopy (cTEM) image of PAnDs containing nanorods (NRs)—plasmonic nanoparticles with high optical absorption cross-section. Scale bar, 100 nm (b) Extinction spectra of as-prepared nanorods and nanorods with a modified surface required for incorporation into PAnDs. The red line represents the optical density spectrum of the gold nanorods as synthesized, while the blue line represents the spectrum of the nanorods after organic surface modification. (c-f) cTEM images of unloaded PAnD and PAnDs with varying compositions (including (d,e) loading with gold nanorods and (f) silver nanoplates with various sizes (200 nm in panel c and d and 400 nm in panels e and f). Scale bars in c,d, 100 nm. Scale bars in e,f, 200 nm.

Figure 11:
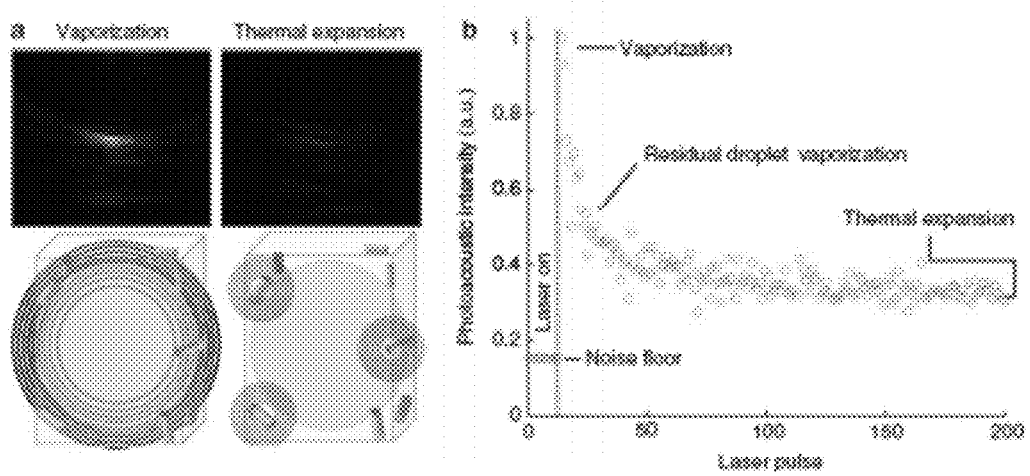

FIG. 11 shows photoacoustic contrast enhancement in vitro. (a) Photoacoustic images reconstructed using vaporization-based and thermal expansion-based signals captured at one location. Each spot size is 1 mm. The schematic diagrams below indicate the associated mechanisms of photoacoustic signal generation. Qualitatively, the vaporization-based image has stronger photoacoustic signal and higher signal-to-noise ratio (SNR) compared to the traditional, thermal expansion-based photoacoustic image. (b) Magnitude of pressure transients, measured as the pulsed laser irradiation continues (i.e., over time), indicating the difference in photoacoustic signal produced by vaporization and thermal expansion mechanisms. The lowest level of signal before laser irradiation is indicative of system noise. Once the pulsed laser irradiation is on, the magnitude of photoacoustic signal is initially dominated by PAnD vaporization. The later, steady-state level of photoacoustic signal is attributed to thermal expansion caused by gold nanorods. In this experimental setup, 50% of the droplets are disrupted by the $8^{th}$ laser pulse. This value, however, is variable depending on several factors including droplet size, extent of nanoparticle loading, laser fluence, optical and properties of the surrounding environment.

Figure 12:
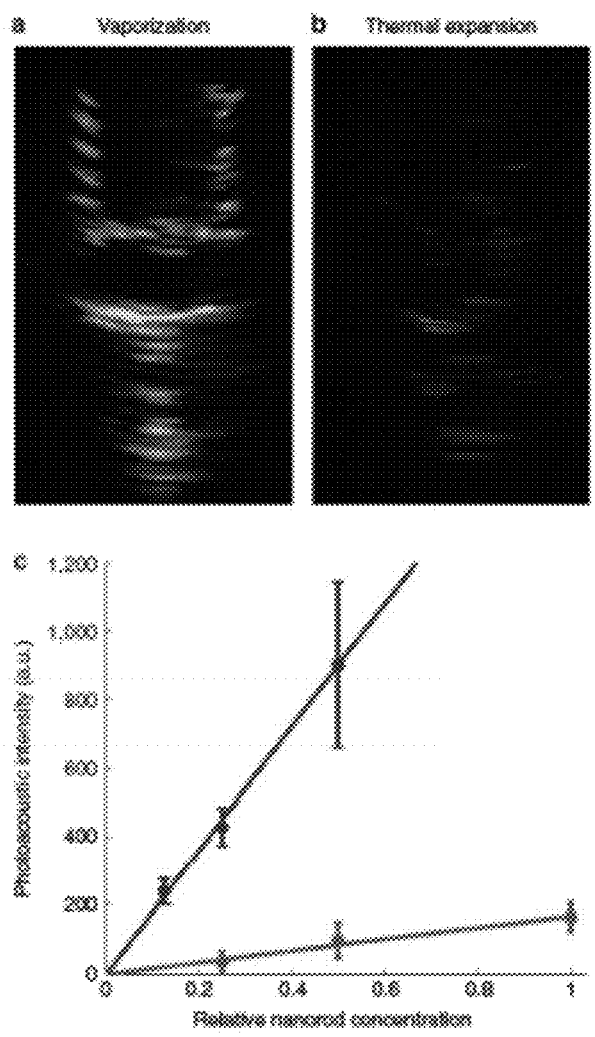

FIG. 12 illustrates photoacoustic imaging in vitro. (a) Photoacoustic images of the laser-beam drawn letters "U" and "T" reconstructed using vaporization-based signals. Both letters stand 1.2 cm tall and 0.5 cm wide. (b) Photoacoustic image of the thermal expansion-based signals over the same area as a. The vaporization-based image has stronger signal and higher signal-to-noise ratio (SNR) compared to the traditional, thermal expansion-based photoacoustic image. (c) Analysis of photoacoustic signal amplitude from PAnDs (blue line) and gold nanorods alone (red line) reveals that for the same concentration of gold nanorods, photoacoustic signal amplitude from 200 nm PAnDs is an order of magnitude higher than the nanorod-assisted photoacoustic signal. Error bars indicate one standard deviation.

Figure 13:
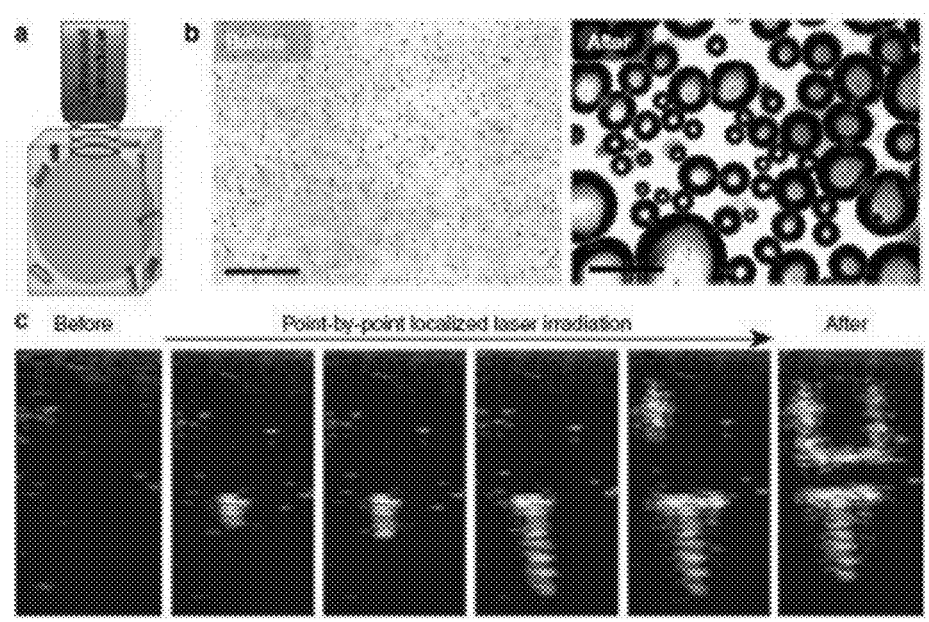

FIG. 13 shows ultrasound contrast enhancement in vitro. (a) Depiction of the gas phase of a PAnD after laser triggered vaporization has occurred. These microbubbles provide significant acoustic impedance mismatch between the PFC gas and the surrounding environment. (b) Optical images of a hydrogel with PAnDs before laser exposure and after laser exposure. Individual droplets are expected to create bubbles approximately 5 time the diameter of the original droplet. The larger bubbles are due to rapid coalescence of smaller bubbles. Scale bars represent 50 µm. (c) Sequential US frames captured as the laser irradiation produced desired pattern in the phantom. The image before laser irradiation illustrates that the ultrasound field alone does not activate PAnDs (i.e., does not initiate the liquid-to-gas transfer of the PFC). As PAnDs are irradiated with laser beam at corresponding positions, the microbubbles are locally triggered, resulting in ultrasound contrast enhancement. Each individual spot is approximately 1 mm, with the final letters standing 1.2 cm tall and 0.5 cm wide. Images are in 20 dB scale.

Figure 14:
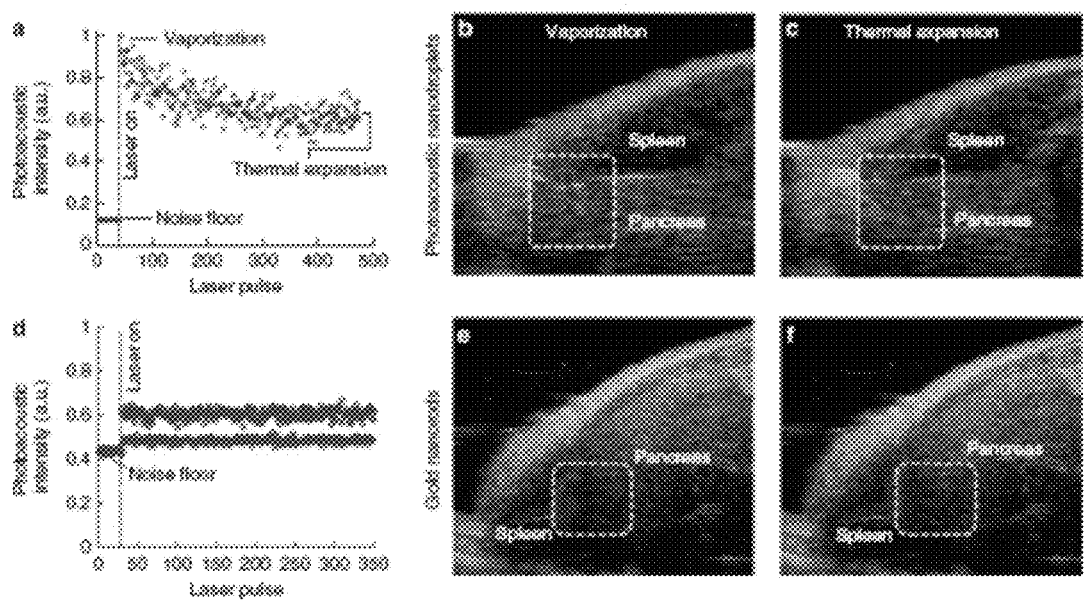

FIG. 14 shows photoacoustic contrast enhancement in vivo. (a) Graph depicting the average photoacoustic intensity within the region of interest corresponding to the injected PAnDs, indicated by boxes in panel b and panel c. Upon pulsed laser irradiation, photoacoustic signal is high and then, with continued pulsed laser irradiation, decays to a steady-state level of thermal expansion-based photoacoustic signal related to the expelled nanorods and endogenous chromophores. Vaporization signal over thermal expansion signal represents a 4.3 dB increase. (b) Combined ultrasound and photoacoustic image of the peak photoacoustic signal generated from the rapid phase transition of the PAnDs. (c) Combined ultrasound and photoacoustic image representing photoacoustic signal generated from expelled gold nanorods and endogenous chromophores. Each frame is 20.4 mm wide by 12.8 mm tall. Ultrasound is in 20 dB scale. In this experimental setup approximately 50% of the droplets are disrupted by the $60^{th}$ laser pulse. (d) Graph displaying changes of photoacoustic signals during continued pulsed laser irradiation before and after an injection of only gold nanorods. The green circles represent photoacoustic signal of the endogenous photoabsorbers in the mouse tissues. Blue circles represent the photoacoustic signal due to thermal expansion caused by both the endogenous photoabsorbers and the injected gold nanorods. It is important to note that there was no significant change of these signals as laser irradiation continued, unlike those signals created by PAnDs. The injection of gold nanorods constituted a 1.9 dB increase in signal. (e,f) Combined photoacoustic and ultrasound images of mouse cross-section and injection site of gold nanorods immediately after the laser was turned on (first laser pulse) and at the end of the laser pulsing (last laser pulse). Note there is insignificant difference between these images (e and f), suggesting a static signal production via thermal expansion. Each image is 12.2 mm wide by 10.8 mm tall. Ultrasound image is displayed using 20 dB scale.

Figure 15:
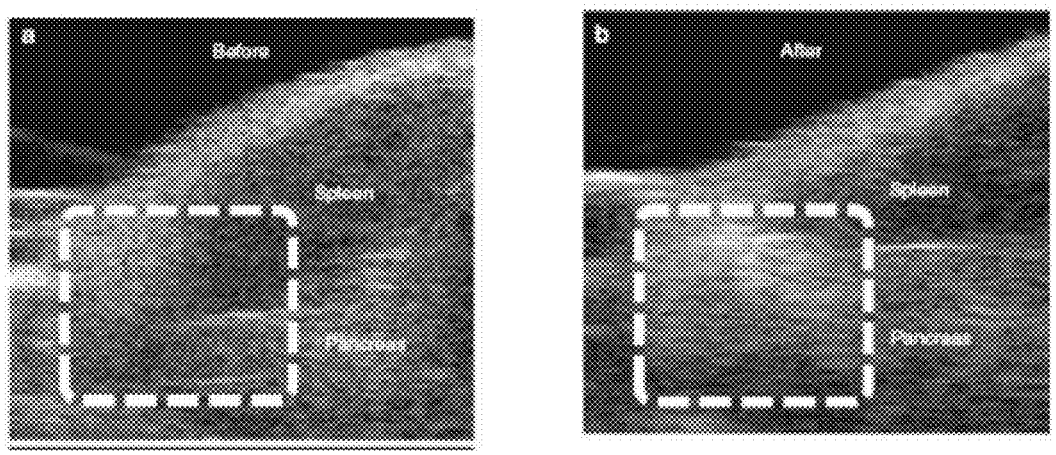

FIG. 15 illustrates ultrasound contrast enhancement in vivo. (a) Ultrasound image of a mouse cross-section before injection of PAnDs displaying the location of the spleen and pancreas. (b) Ultrasound image of the same cross-section after the direct injection and laser activation of PAnDs. The boxes in both images identify the region of interest where PAnDs were injected. The activated PAnDs resulted in an approximately 29 dB increase over the native contrast. Both panels are 13.5 mm wide by 18.1 mm tall and are in 20 dB scale.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure generally relates to nanocarrier compositions and methods of imaging and therapy. More particularly, the present disclosure relates to nanocarrier compositions and methods for selectively imaging and providing therapy to biological tissue.

In accordance with embodiments of the present disclosure, nanocarrier compositions are provided in addition to methods of using nanocarriers for ultrasound and photoacoustic imaging as well as many other imaging and therapeutic applications. In one embodiment, a nanocarrier of the present disclosure comprises an organic liquid core with a plurality of nanoparticles dispersed therein, and a coating material disposed around the exterior surface of the organic liquid core. As used herein, the term "nanocarrier" is not intended to limit the compositions of the present disclosure to any particular size or scale. Rather, nanocarrier compositions of the present disclosure may range in size from about 10 nanometers to 10 micrometers. The nanocarrier compositions of the present disclosure have many potential applications in numerous areas including, but not limited to, drug delivery, diagnostics, therapy and imaging, which will be discussed in more detail below.

One of the many potential advantages of the present disclosure, only some of which are herein disclosed, is that in some embodiments, the size of the nanocarrier may allow for passive diffusion into tumor tissues, and, therefore, may be easily used to image many pathologies. In those embodiments where the nanocarrier is on a smaller scale, the small size may allow the nanocarrier to travel almost anywhere in the body where imaging and/or therapy may need to be performed. For example, embodiments incorporating metal nanoparticles and therapeutic agents may provide nanocarriers that could act as optically triggered drug delivery and drug release systems.

Another advantage of certain embodiments of the present disclosure is a "remotely triggered" functionality. In other words, the system may remain inert in the body until specifically triggered as described in further detail below. Nanocarriers may also be used advantageously in therapeutic applications such as to first target the nanocarriers to a specified location, and then remotely trigger them into an activated state. Sometimes referred to as a "dual targeted delivery system," this feature may minimize the side effects of systemic drugs, microwave ablation therapy, vessel occlusion therapy, photothermal therapy, and nuclear medicine. Nanocarriers of the present disclosure may also be used as contrast enhancement for optical imaging methods (such as optical coherence tomography), magnetic resonance imaging, computed tomography, and photoacoustic imaging (for example, through mechanisms of vaporization and thermal expansion). Additionally, embodiments containing magnetic iron oxide and/or cobalt nanoparticles may provide nanocarriers that can be used in microwave ablation therapy and magnetomotive imaging enhancement.

A. Nanocarrier Compositions

Figure 1:
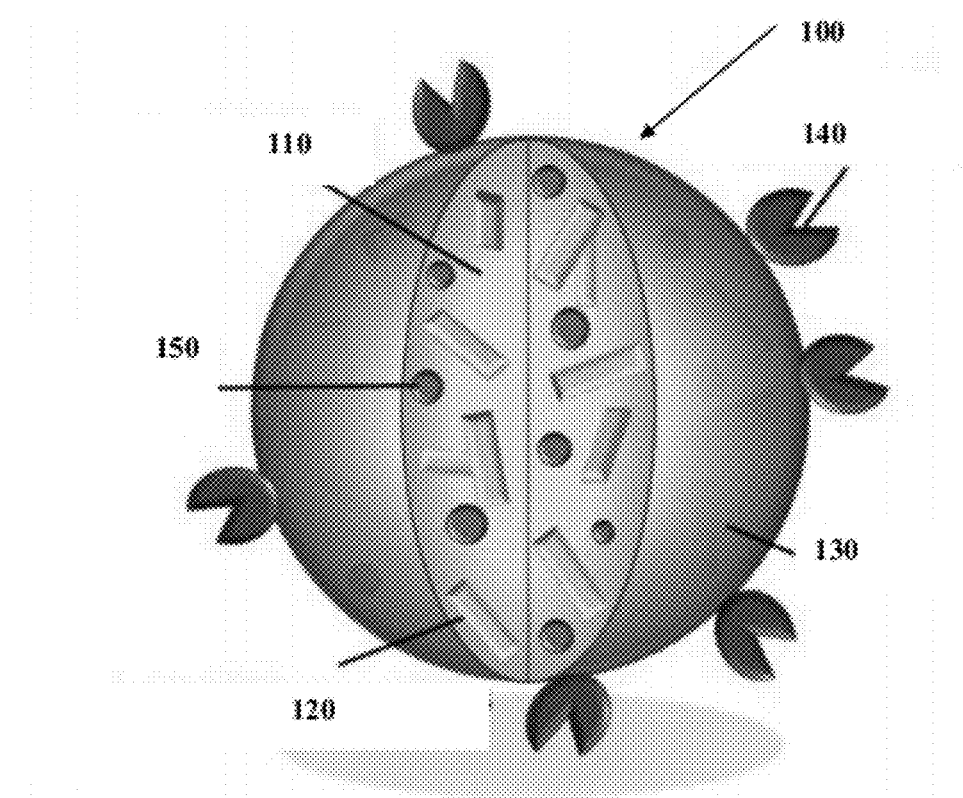
FIG. 1 shows a sketch depicting an example embodiment of a nanocarrier of the present disclosure.

As previously mentioned, a nanocarrier of the present disclosure comprises an organic liquid comprising a plurality of nanoparticles dispersed therein, and a coating material disposed around the exterior surface of the organic liquid. Referring now to FIG. 1, one exemplary embodiment of a nanocarrier of the present disclosure is illustrated. In one embodiment, a nanocarrier 100 may comprise an organic liquid 110 and nanoparticles 120 dispersed in organic liquid 110. Additionally, a nanocarrier of the present disclosure further comprises a coating 130, which surrounds the exterior surface of organic liquid 110. The terms "coat," "coated," or "coating," as used herein, refer to at least a partial coating of the organic liquid. One hundred percent coverage is not necessarily implied by these terms. Optionally, in some embodiments, a nanocarrier of the present disclosure may also comprise a targeting moiety 140 and/or a therapeutic agent 150.

Examples of organic liquids suitable for use in the nanocarriers of the present disclosure may include, but are not limited to, perfluorocarbons. Examples of suitable perfluorocarbons may include, but are not limited to, perfluorocarbons comprising about 5 to about 12 carbons. One specific example of a suitable perfluorocarbon is dodecafluoropentane (DDFP), commercially available from FluoroMed, L.P., Round Rock, Tex. Another example of a suitable perfluorocarbon is perfluororpentane.

As mentioned above, a nanocarrier of the present disclosure further comprises nanoparticles dispersed in the organic liquid. Nanoparticles suitable for use in the present disclosure may comprise any biocompatible metal. Examples of suitable metals include, but are not limited to, copper, iron oxide, cobalt and noble metals, such as gold and/or silver. One of ordinary skill in the art will be able to select of a suitable type of nanoparticle taking into consideration at least the type of imaging and/or therapy to be performed.

In some embodiments, nanoparticles may be included in the organic liquid in an amount less than 2 milligrams per milliliter. In some embodiments, nanoparticles may be included in the organic liquid in an amount less than 10 micrograms per milliliter. When used at this concentration, there are generally no cytotoxic effects due to the nanoparticles.

Further, nanoparticles suitable for use in the nanocarrier compositions of the present disclosure may have an exterior diameter on the order of about 1 nanometers to about 1 micron, while in some embodiments, the diameter may range from about 100 nanometers to about 500 nanometers. The nanoparticles may be any shape, including but not limited to, spheres, rods, shells, plates, crescents, and the like. Furthermore, in some embodiments, the nanoparticles also may have tunable properties so as to resonate in the NIR region. For example, by varying the shape and aspect ratio of nanoparticles, the particles can be manufactured to absorb light at the desired wavelength across a wide spectrum including near infrared spectrum.

In addition to the organic liquid, a nanocarrier composition of the present disclosure further comprises a coating material disposed around the exterior surface of the organic liquid. Examples of suitable coating materials may include, but are not limited to bovine serum albumin (BSA), lipids, polymers, and combinations thereof.

In some embodiments, a nanocarrier composition of the present disclosure may have an exterior diameter on the order of about 10 nanometers to about 10 micrometer, while in some embodiments, the diameter may range from about 10 nanometers to about 1 micrometer. Still further, in some embodiments, a nanocarrier composition may have an exterior diameter from about 10 nanometers to about 500 nanometers.

Optionally, in some embodiments, a nanocarrier composition may further comprise a therapeutic agent. In some embodiments, a therapeutic agent may be included in the organic liquid of the nanocarrier compositions. In some embodiments, a therapeutic agent may be on the surface of the nanocarrier composition, for example, attached to or within the coating material.

In one embodiment, a therapeutic agent may be an anti-cancer agent. Any suitable anti-cancer agent may be used in the compositions and methods of the present disclosure. The selection of a suitable anti-cancer agent may depend upon, among other things, the type of cancer to be treated and the composition of the nanocarrier compositions of the present disclosure. In certain embodiments, the anti-cancer agent may be effective for treating one or more of pancreatic cancer, esophageal cancer, rectal cancer, colon cancer, prostate cancer, kidney cancer, liver cancer, breast cancer, ovarian cancer, and stomach cancer. In certain embodiments, the anti-cancer agent may be, but is not limited to, gemcitabine, doxorubicin, 5-Fu, or paclitaxel.

In certain embodiments, the anti-cancer agent may be a prodrug form of an anti-cancer agent. As used herein, the term "prodrug form" and its derivatives is used to refer to a drug that has been chemically modified to add and/or remove one or more substituents in such a manner that, upon introduction of the prodrug form into a subject, such a modification may be reversed by naturally occurring processes, thus reproducing the drug. The use of a prodrug form of an anti-cancer agent in the compositions and methods of the present disclosure, among other things, may increase the concentration of the anti-cancer agent in the compositions and methods of the present disclosure. In certain embodiments, an anti-cancer agent may be chemically modified with an alkyl or acyl group or some form of lipid. The selection of such a chemical modification, including the substituent(s) to add and/or remove to create the prodrug, may depend upon a number of factors including, but not limited to, the particular drug and the desired properties of the prodrug. One of ordinary skill in the art, with the benefit of this disclosure, will recognize suitable chemical modifications.

Furthermore, in some embodiments, a nanocarrier composition of the present disclosure may optionally comprise a targeting moiety. The targeting moieties useful in the compositions and methods of the present disclosure include molecules that may be bound to an exterior surface of a nanocarrier composition and which recognize a particular site of interest in a subject. In certain embodiments, the targeting moieties may be bound directly to the coating material or bound to the coating material using a linking molecule.

In certain embodiments, the targeting moiety may be chosen, among other things, to at least partially increase the uptake of the compositions of the present disclosure into a desired cell and/or tissue type when introduced into a subject. In certain embodiments, the targeting moiety may recognize a particular ligand or receptor present in a desired cell and/or tissue type when introduced into a subject. In certain embodiments, the targeting moiety may be an antibody that recognizes such a particular ligand or receptor. The use of antibody fragments may also be suitable in the compositions and methods of the present disclosure. The choice of a targeting moiety may depend upon, among other things, the cell and/or tissue type into which an at least partial increase in uptake of the compositions of the present disclosure is desired, as well as particular ligand(s) present in such cell and/or tissue types. In certain embodiments, the targeting moiety may be a moiety that recognizes a molecule which is present in higher amounts in an abnormal form of a tissue when compared to a normal form of the same tissue (i.e., the molecule is "up-regulated" in the abnormal form of the tissue). For example, in certain embodiments, antibodies which bind to epidermal growth factor (EGFR) may be suitable for use in the compositions and methods of the present disclosure when it is desired to at least partially increase the uptake of the compositions of the present disclosure into cancerous epithelial tissue. As a further example, antibodies such as anti-Claudin-4, anti-Muc1, or anti-EGFR may be suitable for use in the compositions and methods of the present disclosure when it is desired to at least partially increase the uptake of the compositions of the present disclosure into cancerous pancreatic tissue. In some embodiments, a suitable targeting moiety may be a peptide sequence, DNA fragment, aptamer, RNA, folate, polymer, etc. One of ordinary skill in the art, with the benefit of this disclosure, will recognize other targeting moieties that may be useful in the compositions and methods of the present disclosure. Such targeting moieties are considered to be within the spirit of the present disclosure.

As mentioned above, in certain embodiments, the targeting moieties useful in the compositions and methods of the present disclosure may be bound directly to the coating material. In certain embodiments, the targeting moieties useful in the compositions and methods of the present disclosure may be bound to the coating material via a linking molecule. The linking molecules useful in the compositions and methods of the present disclosure may be any molecule capable of binding to both the coating material used in the compositions and methods of the present disclosure and the targeting moieties used in the compositions and methods of the present disclosure. In certain embodiments, the linking molecule may be a hydrophilic polymer. Suitable linking molecules include, but are not limited to, poly(ethylene glycol) and its derivatives, dithiol compounds, dithiol compounds with hydrazide and/or carboxylic functionality, or single thiols and/or amines or their derivatives. In certain embodiments, the linking molecule and the targeting moiety may be bound by one or more covalent bonds. In certain embodiments, the linking molecule, in addition to linking the targeting moiety and the coating material, may impart certain benefits upon the compositions of the present disclosure, including, but not limited to, improved hydrophilicity and stability in solution, reduced immunogenic responses upon introduction of the compositions of the present disclosure into a subject, increased circulation time of the compositions of the present disclosure when introduced into the bloodstream of a subject. The choice of a linking molecule may depend upon, among other things, the targeting moiety chosen and the subject into which the compositions of the present invention are to be introduced. One of ordinary skill in the art, with the benefit of this disclosure, will recognize additional suitable linking molecules. Such linking molecules are considered to be within the spirit of the present disclosure.

In some embodiments, nanocarrier compositions of the present disclosure may further comprise gene components, such as siRNA or therapeutic DNA fragments. In some embodiments, a gene component may be included in the organic liquid of the nanocarrier compositions. In some embodiments, a gene component may be on the surface of the nanocarrier composition, for example, attached to or within the coating material. These agents may be used for gene therapy or to enhance sensitivity in drug resistant cell lines.

B. Methods of Use and Preparation

The nanocarrier compositions of the present disclosure have many potential applications in numerous areas including, but not limited to, drug delivery, diagnostics, therapy and imaging.

In one embodiment, the present disclosure provides a method of imaging comprising providing a nanocarrier composition comprising: an organic liquid comprising a plurality of nanoparticles dispersed therein, and a coating material disposed around the exterior surface of the organic liquid; and imaging a biological tissue comprising the nanocarrier composition. In another embodiment, the present disclosure provides a therapeutic method comprising contacting a biological tissue with a nanocarrier composition comprising: an organic liquid comprising a plurality of nanoparticles dispersed therein, a coating material disposed around the exterior surface of the organic liquid, and a therapeutic agent.

In some embodiments, the nanocarrier compositions of the present disclosure may act as a contrast agent for continuous wave photoacoustic imaging, combined photoacoustic and ultrasound imaging, magnetomotive imaging, optical coherent tomography, magnetic resonance imaging, computed tomography, nuclear imaging modalities or any combination thereof. Furthermore, when the nanocarriers contain magnetic iron oxide and/or cobalt nanoparticles, they may be used in microwave ablation therapy and magnetomotive imaging enhancement.

In one embodiment, nanoparticles dispersed within the organic liquid may absorb light energy typically employed during photoacoustic imaging techniques. Therefore, the nanoparticles may act in their traditional role as photoacoustic contrast agents. Simultaneously, the absorption of that light energy by the nanoparticles may cause them to heat, thereby "activating" the organic liquid as an ultrasound contrast agent, for example, by vaporizing the organic liquid. This activation may create an impedance mismatch between the organic gas (from the vaporized organic liquid) and the surrounding blood and tissues, providing strong ultrasound imaging contrast. Therefore, the nanocarrier compositions may act as a contrast agent for photoacoustic imaging at the cellular level in two ways: (1) absorption from the nanoparticles, and (2) extra induced pressure waves generated by the vaporization of the organic liquid.

Similarly, in some embodiments, nanocarriers of the present disclosure may be "remotely triggered" by applying energy to the nanocarrier composition. In some embodiments, energy such as an electromagnetic field, optical methods, or specific radiofrequencies may be applied to biological tissue thereby causing the vaporization of the organic liquid and if the nanocarrier further comprises a therapeutic agent, the release of the therapeutic agent. In some embodiments, this may provide a clinician the ability to control and visualize drug therapy noninvasively.

Some embodiments of the present disclosure provide methods of using nanocarriers to detect the size and proper boundaries of tumor regions. In one embodiment, nanocarrier compositions of the present disclosure may be delivered to cancerous tissue. Delivery methods may include patient injection of nanocarriers, and may also include using targeting moieties to help facilitate accumulation in a diseased tissue. Kumar et al. (2008), Korpanty et al. (2005), Byrne et al. (2008). It is believed that this method may provide two or more mechanisms of enhancing diagnostic imaging contrast. When used in conjunction with a combined photoacoustic and ultrasound imaging system, the nanocarriers may strengthen photoacoustic signals from the tumor region while simultaneously increasing ultrasound contrast. When iron oxide nanoparticles are included in the nanocarriers, magnetic resonance imaging, and photoacoustic and/or ultrasound imaging may be used in conjunction. Therefore, two or more imaging modalities may be used by clinicians to verify the location and size of diseased tissue by using a simple injection of nanocarriers.

Additionally, according to embodiments of the present invention, nanocarriers comprising both therapeutic agents and targeting moieties may act as a targeted delivery system for therapeutic agents.

Some embodiments provide methods for the use of the organic gas bubbles as vascular blocking agents to initiate necrosis in a specific location of tissue (e.g. blocking tumor vasculature). In some embodiments, deposition of nanocarriers at the region of necrosis would permit photoacoustical monitoring of the decay.

Some embodiments of the present disclosure provide methods for preparing nanocarrier compositions of the present disclosure. In one embodiment, a nanocarrier of the present disclosure may be synthesized through a "organic liquid in water" emulsion. For example, a coating material, such as BSA, may be dissolved in water and aqueous nanoparticles may undergo a process of phase transfer by recapping in hydrocarbon thiols, octadecylamine (ODA), etc. The phase transferred nanoparticles may then be dispersed into the organic liquid. The two solutions may then be combined and sonicated.

To facilitate a better understanding of the present invention, the following examples of certain aspects of some embodiments are given. In no way should the following examples be read to limit, or define, the scope of the invention.

EXAMPLES

Exogenous contrast in photoacoustic imaging can be achieved through use of contrast agents, such as plasmonic metal nanoparticles. These nanoparticles have optical absorption cross-sections that are orders of magnitude higher than those of tissue components and are generally used to enhance the optical absorption of nanoparticle labeled tissues. Surface-functionalized nanoparticles also provide molecular functionality with the addition of specific targeting moieties. However, the production of photoacoustic transients using these exogenous agents is still governed by thermal expansion, and therefore, the same fundamental limits of this mode of photoacoustic signal generation apply.

Exogenous contrast agents have also been designed and developed for ultrasound contrast enhancement. Gas microbubbles, for instance, have long been used in diagnostic ultrasound imaging as highly sensitive, cost effective, and biocompatible contrast agents. Due to their highly scattering acoustic properties and nonlinear interactions with incident ultrasound, microbubbles are used in many clinical applications including assessment of coronary artery disease, hyperlipidaemia, angiogenesis, inflammation, and tumor formation. Microbubbles can also be used to assess therapeutic strategies and to facilitate delivery and release of therapeutic agents based on physical interactions of microbubbles with ultrasound. Furthermore, current research is focused on adapting the microbubbles, through surface modifications, cargo encapsulation or attachment, and other modifications, to allow for additional therapeutic applications. Therefore, microbubbles are a sensitive contrast agent that has diagnostic and therapeutic effects for vascular applications.

Microbubbles do have limitations, however. Gas diffusion and biological clearance significantly limit their circulation time and therefore, any potential therapeutic effects through cellular targeting and chemical or physical treatment. Furthermore, due to their size (>1 micrometer), microbubble effects are limited to within the vascular system. The invention of phase shift PFC liquid droplets and acoustic droplet vaporization (ADV) provided a method to solve both these problems. Liquid droplets of PFCs, often stabilized with albumin, lipids, or polymers, provide a long circulating, triggerable contrast agent. The use of PFCs with boiling points below body temperature (37° C.) allow these agents to become superheated and easily vaporize in the presence of pulsed ultrasound with frequencies and pressures in the sub-therapeutic range. However, for tumor imaging, molecular diagnosis, and therapy, these particles would have to extravasate out of the vasculature into the tumor interstitial space where cellular interactions could take place. To facilitate these cellular interactions, the phase change agents would have to be smaller than the known endothelial gap junction sizes of up to 800 nm in tumor vasculature. The gap junction size depends strongly on tumor type and location, but sizes between 300 nm to 800 nm have been suggested, and thus, passive accumulation of nanoparticles in tumors, entitled the enhanced permeability and retention effect (EPR), can occur with nanoparticles smaller than the junction size.

While nanoscale PFC droplets can be easily synthesized, their inherent acoustic contrast is minimal (contrast enhancement through Rayleigh scattering of sound). Large acoustic contrast from these nanoscale PFC droplets occurs only when they undergo a phase transition into a gaseous state. Studies have revealed that ADV requires increased acoustic input as the diameter of the droplets decreases (due to decreased surface tension and increased boiling point) and the frequency of the transducer decreases. The extra acoustic input energy is required for ADV since smaller droplets have significantly higher surface tension to overcome. Combined with surface stabilizing agents (protein, lipids, and polymers) these particles become difficult to vaporize with typical diagnostic ultrasound frequencies and pressures. Therefore, acoustic nanodroplet vaporization (AnDV) may require acoustic frequencies and pressures that will also cause unwanted bioeffects. Hence, a methodology to activate PFC nanodroplets without unwanted bioeffects is desired.

We have developed an optically activated, nanoscale dual contrast agent for combined photoacoustic and ultrasound contrast enhanced imaging. Photoacoustic nanoDroplets (PAnDs) consist of a droplet of liquid PFC with a bovine serum albumin (BSA) shell in which optically absorbing nanoparticles have been suspended. These droplets use optical absorption for several purposes including a mechanism to trigger the liquid-to-gas transition of a nanoscale PFC droplet, the production of strong photoacoustic signal through vaporization, and prolonged thermal expansion signal via the encapsulated optically absorbing nanoparticles. The resulting gaseous phase of the PFC increases acoustic impedance mismatch for increased ultrasound signal. Therefore, PAnDs comprise three contrast mechanisms simultaneously, offer an environment easily modified for molecular targeting and therapeutic cargo delivery, and provide the opportunity to use the photoacoustic contrast mechanism, vaporization, safely in biological tissues.

In the following examples, synthesis, characterization, and utility of PAnDs for photoacoustic and ultrasound imaging is discussed. Using hydrogel phantoms, both ultrasound and photoacoustic imaging of the PAnDs was performed to determine and quantify the contrast enhancement from PAnDs. It was demonstrated that PAnDs provide three mechanisms of contrast: vaporization and thermal expansion for photoacoustics, and increased acoustic impedance mismatch for ultrasound. Furthermore, PAnDs were employed in an in vivo murine model to validate the contrast enhancing effects in highly optically scattering and absorbing tissues. Therefore, vaporization as a photoacoustic phenomenon was introduced at biologically safe levels of laser energy, and the ability of PAnDs to act as an optically triggered dual photoacoustic and ultrasound contrast agent was established.

Example 1

Nanocarrier Preparation

Eight samples of bovine serum albumin (BSA) solution were prepared as reflected in Table 1.

TABLE 1

| Sample | Concentration | 2 mg/ml BSA solution (µl) | Deionized H$_2$O (µl) | Total |
| --- | --- | --- | --- | --- |
| 1 | 0.05 mg/ml | 25 | 975 | 1000 |
| 2 | 0.1 mg/ml | 50 | 950 | 1000 |
| 3 | 0.2 mg/ml | 100 | 900 | 1000 |
| 4 | 0.4 mg/ml | 200 | 800 | 1000 |
| 5 | 0.6 mg/ml | 300 | 700 | 1000 |
| 6 | 0.8 mg/ml | 400 | 600 | 1000 |
| 7 | 1.0 mg/ml | 500 | 500 | 1000 |
| 8 | 2.0 mg/ml | 1000 | 0 | 1000 |

An organic liquid, dodecafluoropentane ($C_5F_{12}$), was added to each sample in the amount of about 111 µl per sample. Each sample was sonicated for about 1 minute. To allow for microscopy imaging, each sample was diluted in ratios of about 1:10-1:100.

Figure 2A:
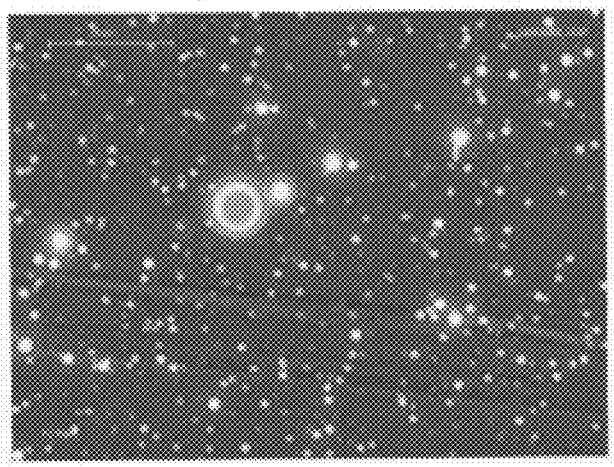
FIGS. 2A, 2B and 2C show raw and processed images of an example embodiment of a nanocarrier of the present disclosure.
Figure 2B:
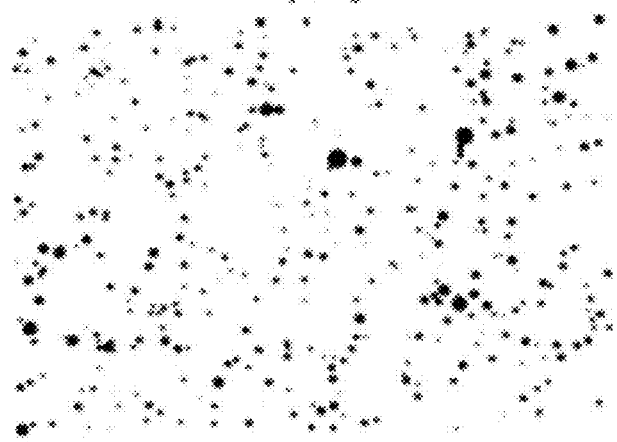
Figure 2C:
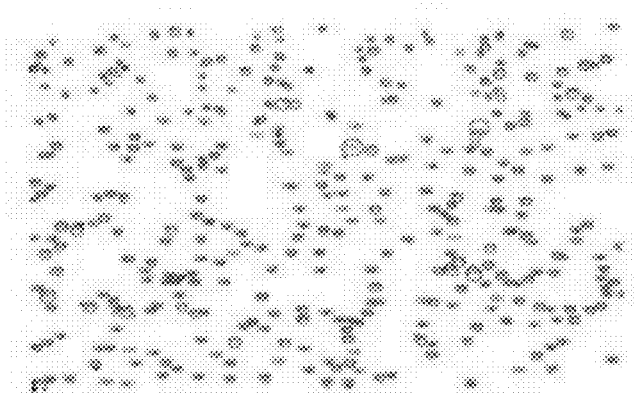
Figure 3A:
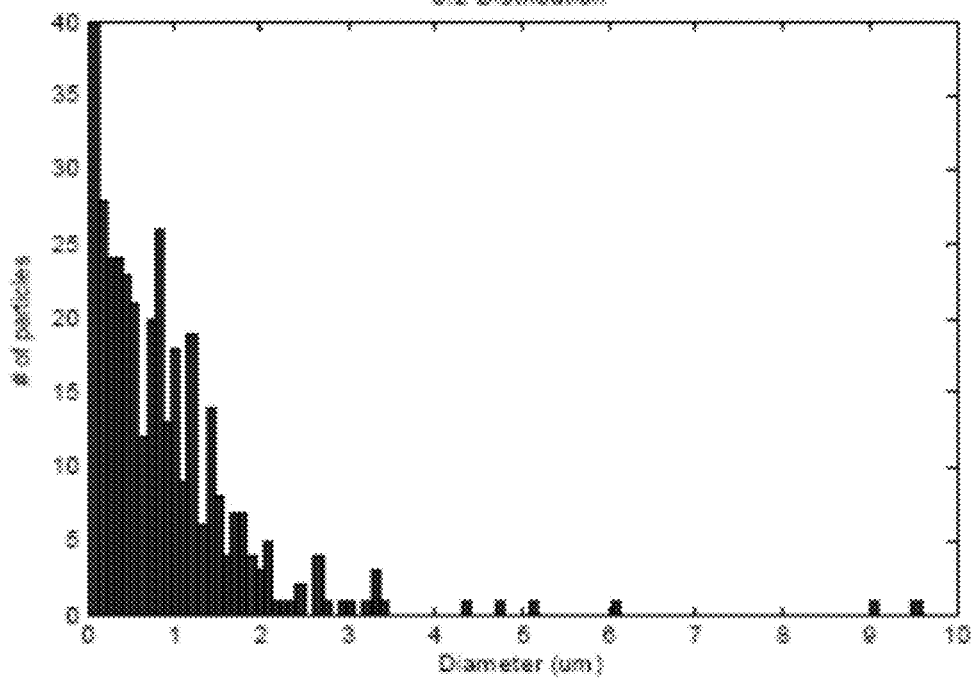
FIGS. 3A and 3B illustrate size distributions of an example embodiment of a nanocarrier of the present disclosure.
Figure 3B:
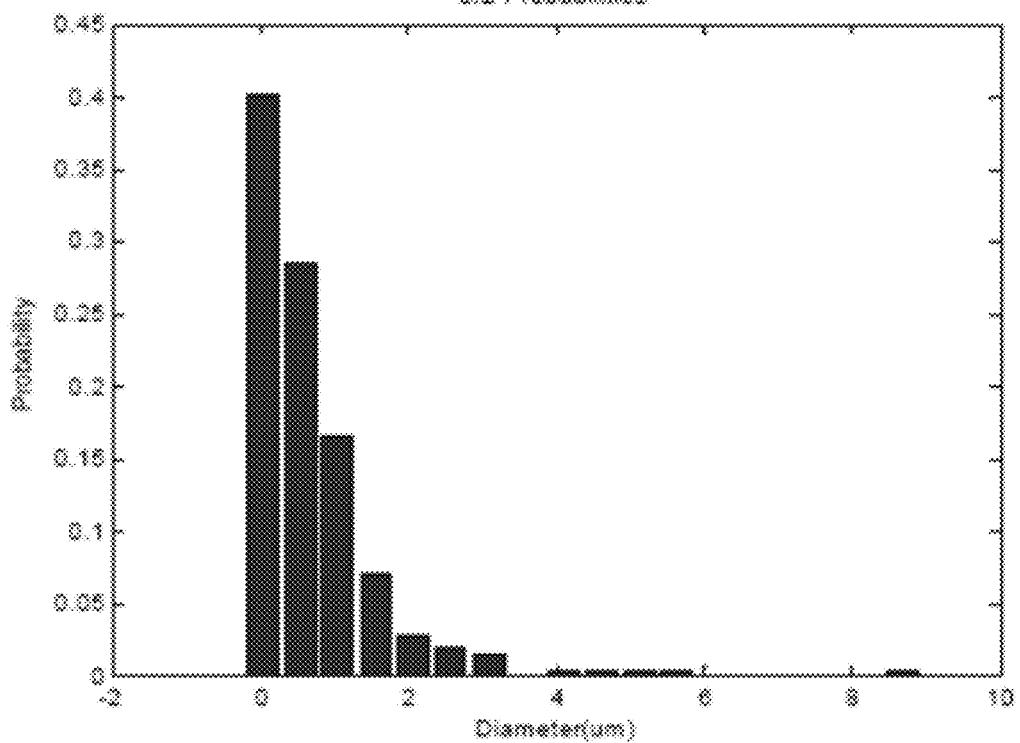

The image data was analyzed using ImageJ software, currently downloadable as freeware from http://rsb.info.nih.gov/ij/. As illustrated in FIGS. 2A-2C, the microscopy images were converted to binary, the outlines of each nanocarrier was numbered, and the area inside each was calculated based of the known length of the scale bar. Assuming each nanocarrier to be a sphere, the diameter was calculated. The bar chart of FIG. 3A shows that most of the nanocarriers are <500 nanometers in diameter. The bar chart of FIG. 3B shows that the nanocarriers have an 80% chance of being less than 500 nanometers in size. If desired, larger nanocarriers may be filtered out.

Example 2

Images of Nanocarrier Compositions

An ~0.0002 M octadecylamine/hexane solution was prepared with about 10 ml of hexane and about 4 mg of ODA. About 2 ml of this solution was placed on top of about 2 ml of a prepared silver nanodiscs solution in a plastic vial. The vial was then capped and shaken vigorously until the phase transfer was complete.

As in Example 1, samples of bovine serum albumin (BSA) solution were prepared as reflected in Table 2.

TABLE 2

| Concentration | 2 mg/ml BSA solution (µl) | Deionized H$_2$O (µl) | Total |
| --- | --- | --- | --- |
| 0.2 mg/ml | 200 | 1800 | 2000 |

Dodecafluoropentane ($C_5F_{12}$) was added in the amount of about 222 µl. The sample was sonicated for about 1 minute. STEM images were taken.

Figure 4A:
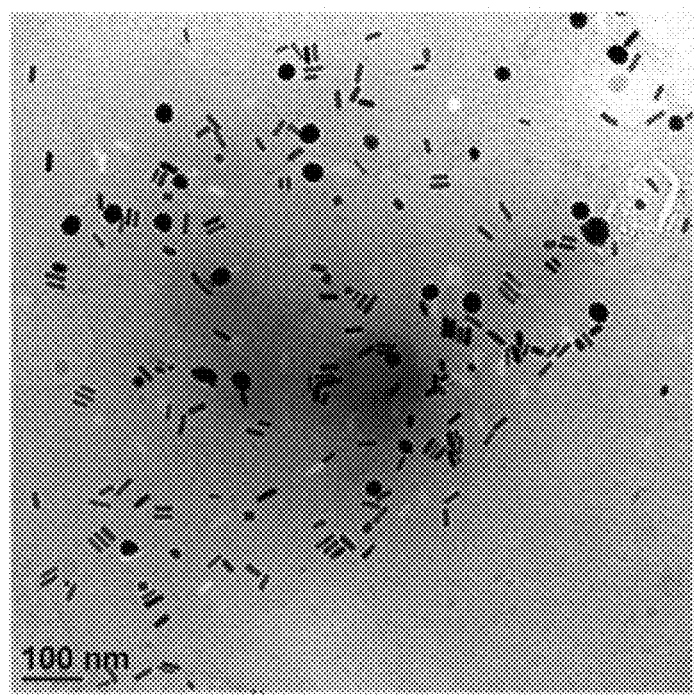
FIGS. 4A and 4B illustrate images of nanoparticles which may be used in an embodiment of the present disclosure.
Figure 4B:
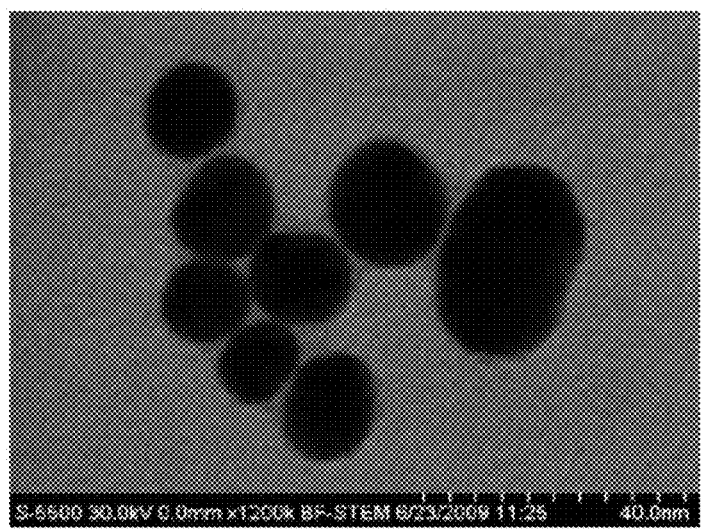

FIGS. 4A and 4B illustrate the images of just the nanoparticles. FIG. 4A is gold nanorods approximately 10 by 40 nm in size. FIG. 4B is gold nanospheres approximately 20 nm in diameter. These figures illustrate the distinctive shapes of these particles, making them relatively easy to find in transmission electron microscopy (TEM) images.

Figure 5A:
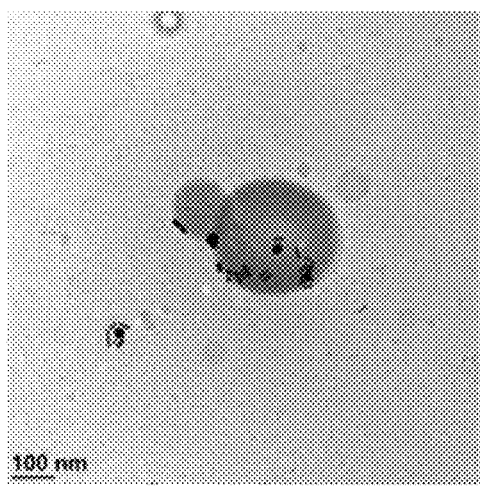
FIGS. 5A, 5B and 5C illustrate images of an example embodiment of the present disclosure.
Figure 5B:
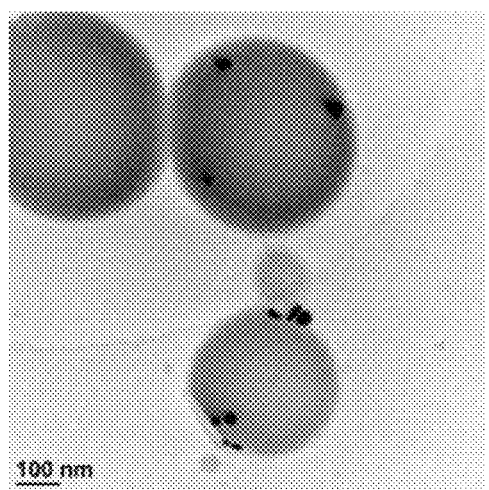
Figure 5C:
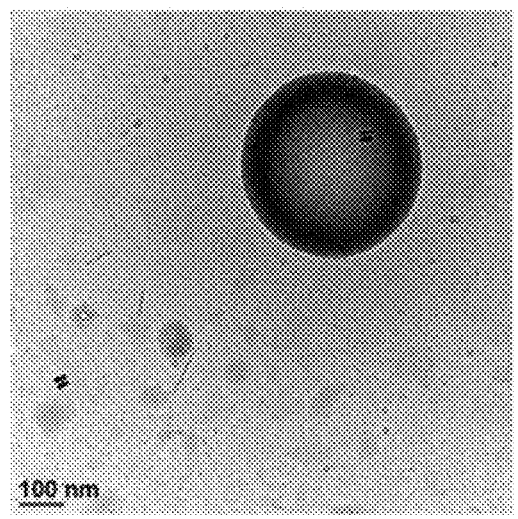

The images of FIGS. 5A-5C show nanocarrier compositions comprising nanoparticles. FIG. 5A shows a nanocarrier comprising gold nanorods approximately 10 by 40 nm in size. FIG. 5B shows a nanocarrier comprising silver nanotriangles, approximately 50 nm on one side. FIG. 5C shows a nanocarrier comprising two gold nanorods approximately 10 by 40 nm in size.

Figure 6A:
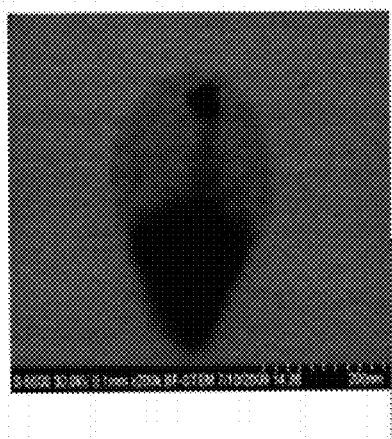
FIGS. 6A, 6B and 6C illustrate STEM images of an example embodiment of the present disclosure.
Figure 6B:
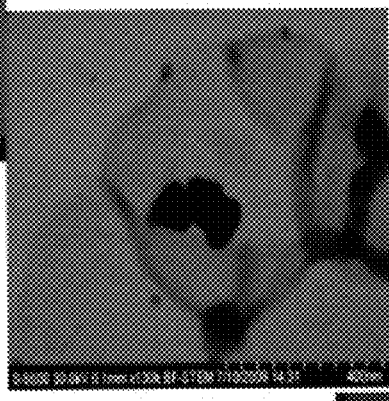
Figure 6C:
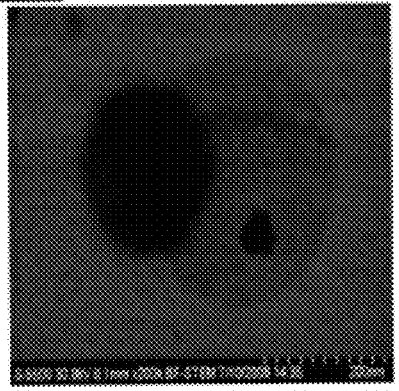

The images of FIGS. 6A-6C illustrate the very obviously shaped nanoparticles within the nanocarriers.

Example 3

Nanocarrier in PA Phantom with Applied Laser

An ~0.0002 M octadecylamine/hexane solution was prepared with about 10 ml of hexane and about 2 mg of ODA. About 2 ml of this solution was placed on top of about 2 ml of a prepared gold nanosphere solution in a plastic vial, wherein the nanospheres had diameters of about 20 nm. The vial was then capped and shaken vigorously until the phase transfer was complete.

As in Example 1, samples of bovine serum albumin (BSA) solution were prepared as reflected in Table 3.

TABLE 3

| Concentration | 2 mg/ml BSA solution (µl) | Deionized $H_2O$ (µl) | Total |
|---|---|---|---|
| 0.2 mg/ml | 200 | 1800 | 2000 |

Dodecafluoropentane ($C_5F_{12}$) was added in the amount of about 222 µl. The sample was sonicated for about 1 minute. STEM images were taken.

To create a phantom, a 10% w/v solution of bis-acrylamide and water was prepared. The solution was vacuumed three or four times until it appeared bubble-free. The nanocarriers were added into the inclusion space (~1 ml/5 ml of gel). Crosslinkers TEMED and 10% APS were added in concentrations of about 0.75 and 5 µl per ml of gel. The mixture was allowed to solidify and stored in a plastic bag in a refrigerator.

Ultrasound images were taken with a winprobe 7 MHz transducer both before and after exposure to photoacoustic imaging using an air beam 532 nm Polaris laser.

Figure 7A:
FIGS. 7A, 7B, 7C and 7D illustrate ultrasound and photoacoustic images of an example embodiment of the present disclosure.
Figure 7B:
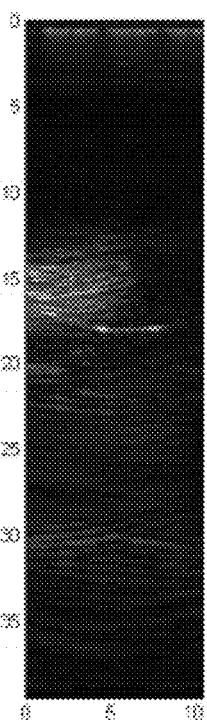
Figure 7C:
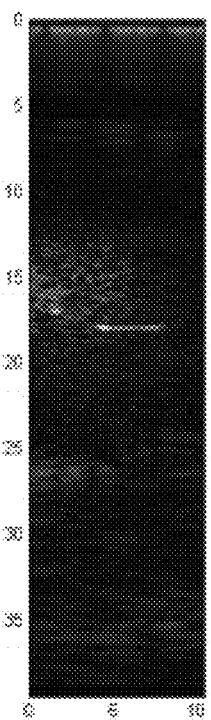
Figure 7D:
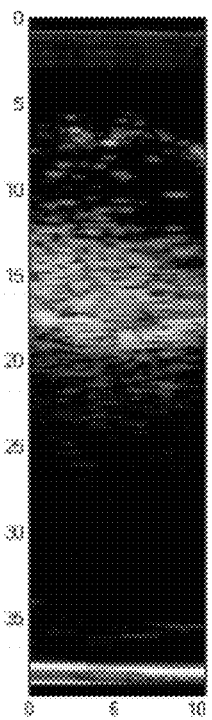

FIG. 7A illustrates the original ultrasound image of the inclusion with the nanocarriers comprising gold nanospheres. The outline of the inclusion is just visible due to a few trapped air bubbles during the inclusion solidification. FIG. 7B illustrates the first photoacoustic imaging frame. Clearly, the highest signal correlates with the location of the inclusion. It is in the lower half of the inclusion because the air beam of the laser was focused in the lower half of the inclusion. FIG. 7C illustrates the second frame of the photoacoustic imaging. The signal is lowered because the initial organic liquid vaporization has occurred, and the signal is coming only from the nanospheres. FIG. 7D illustrates the "after" ultrasound image. It is clearly shown the ultrasound contrast is greatly increased in the area that photoacoustic signal was seen and where the laser beam was focused. These images show that these nanocarriers may act as both ultrasound and photoacoustic contrast agents, they may be remotely triggerable with laser irradiation, and that they may cause photoacoustic signal with the initial vaporization of the nanocarriers.

Example 4

Cytotoxicity was measured using a MTS assay. This assay measured the reducing potential of the cell using a colorimetric reaction, wherein viable cells reduced the MTS reagent to a colored formazan product. The test was run in (A431 (epidermoid carcinoma) and MBA-MD-231 (breast adenocarcinoma) cells. Both the organic liquid and the gold nanospheres combined with two references had a p value<0.05.

The (A431 (epidermoid carcinoma) and MBA-MD-231 (breast adenocarcinoma) cells were grown in a T75 flask to form a 80% confluent cell layer. The cell media was removed by vacuum aspiration. The cells were washed with 5 ml of DPBS without Ca/Mg to remove any remaining media. After swirling, the DPBS was removed with vacuum aspiration. 4 ml of trypsin/EDTA was added and swirled to cover the whole surface. The cells were incubated until they disassociated off the plate.

About 6 ml of media (containing serum) was added to stop the process of trypsinization. The cell suspension was gently pipetted in and out a few times to disaggregate cells. About 1 mL of the suspension was transferred to a 15 mL tube and centrifuged at about 250 rcf for about 5 minutes. The media was removed by vacuum aspiration. About 2 mL of new media was added, and the cell suspension was pipetted in and out a few times to disaggregate cells.

In a new 15 mL tube, about 9 mL of media was placed, and about 1 mL of the cell suspension (roughly 50,000 cells/mL) was added. Less than about 20 µL of the suspension was and placed in both sides of a hemacytometer to counts cells and determine the concentration of cells in suspension.

In a sterile well, the cell suspension was diluted with media sufficient to make about 5000 cells/100 µL (this equates to about 50,000 cells per mL). The cells in the internal wells of the 96 well plate were seeded using a 8 or 12 channel pipetter, with a goal of putting about 5000 cells in each well of the 96 well plate with a total of about 100 µL volume. The cells were then incubated at about 37° C. and about 5% $CO_2$ for about 24 hours.

In order to mix the nanoparticles with the cells, varying concentrations of nanoparticles were prepared. The media was removed via vacuum aspiration in each well. New media incorporating varying concentrations of particles replaced the old media. The cells were then incubated at about 37° C. and about 5% $CO_2$ for about 24 hours.

To perform the MTS assay, the absorbance in each well was measured in both plates at about 490, 600, and 700 nm. About 20 µL of the MTS formazan product was added to each well, and each was incubated at about 37° C. and about 5% $CO_2$ for about 1-4 hours.

Figure 8:
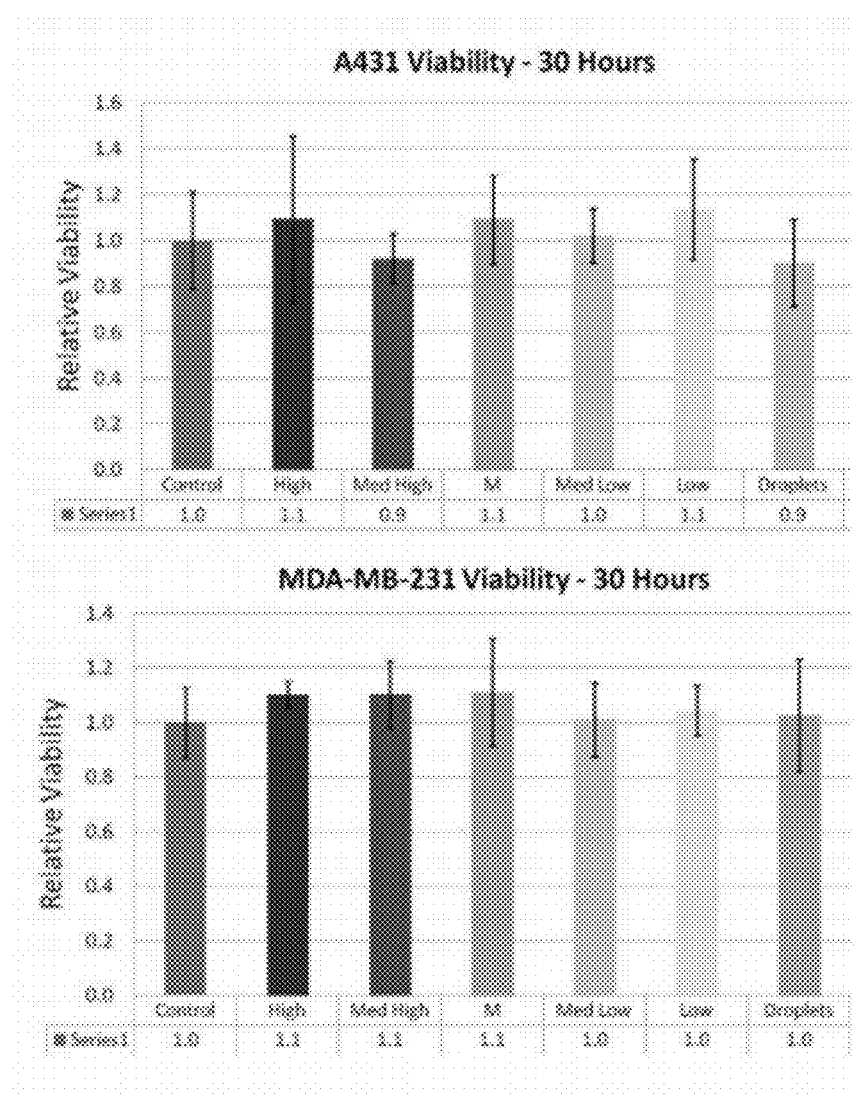
FIG. 8 illustrates the results of a MTS Assay of an example embodiment of a nanocarrier of the present disclosure tested in two cell types. High, Med High to low correspond to the concentration of the nanodroplets used. "droplets" refers to droplets without an gold nanoparticles included, and control is cells only.

A plate reader was used to measure the absorbance in each well at about 490, 600, and 700 nm. The results are illustrated in FIG. 8.

Example 5

Synthesis of Photoacoustic Nanodroplets (PanDs)

Synthesis of the remotely triggered photoacoustic nanodroplets (PanDs) occurred in three steps. First, plasmonic nanoparticles were synthesized and surface modified to allow solubility in organic solvents. Second, the surface modified plasmonic nanoparticles were resuspended in liquid PFC. Finally, the liquid PFC was emulsified with a BSA solution, and the PAnDs were sized using a lipid mini extruder. This procedure created stable, nano-sized PAnDs to be used for ultrasound and photoacoustic imaging.

Methods for synthesis of different plasmonic nanoparticles were adopted from the corresponding original synthesis procedures (Nikoobakht et al., 2003; Thierry et al., 2009; and Zou et al., 2007). Silver nanoplates were synthesized through reduction of silver ions by ascorbic acid (Ledwith et al., 2007). The nanoparticle of focus, gold nanorods, were synthesized first using a slightly modified seed mediated growth method. To make the gold nanorods and silver nanoplates soluble in an organic environment, a two-step ligand exchange method was adopted with slight modifications. Specifically, 5 ml of thiolated poly(ethylene glycol) (mPEG-SH, 5000 Da, Laysan Bio) in water (2.0 mg/ml) and 5 ml of as synthesized gold nanorods (40 nm by 10 nm) were sonicated for 2 minutes and left to react at room temperature for 2 hours. The solution was centrifuged at 10,000 rcf for 10 minutes and the supernatant was removed. The nanorods were redispersed in 5 ml of tetrahydrofuran (THF, Sigma Aldrich). Next, 5 ml of ethanolic dodecanethiol (Sigma Aldrich, 1.0 mg/ml) was added to the THF-nanorod solution and sonicated at room temperature for 30 minutes. The temperature was increased to 50° C. for an additional 60 minutes of sonication. The solution was then left to rest overnight. The solution was then centrifuged at 10,000 rcf for 10 minutes and the supernatant was discarded. The dodecanethiol capped nanorods were resuspended in chloroform. To synthesize the photoacoustic droplets, first 1 ml of as prepared gold nanorods in chloroform were placed into a 7 ml glass scintillation vial. The organic solvent was completely evaporated, leaving dried nanorods on the bottom of a glass vial. Then, 0.25 ml of liquid perfluoropentane (PFP, Fluoromed, Inc.) was added to the vial and sonicated for 2 minutes using a bath sonicator. Next, 2 ml of BSA (Sigma) in saline was added (0.2 mg/ml), and the two solutions were sonicated to produce a colored (pink), opaque emulsion of the PAnDs in the water phase. The PAnDs were then extruded using a lipid extrusion system through polycarbonate membranes (Avanti Polar Lipids) with a 200 nm pore size. This extrusion yielded a $10^8$ PAnD/ml solution.

Three methods were used to characterize the PAnDs. First, ultraviolet to visible spectrophotometry (DU640, Beckman Coulter) was used to study the optical extinction of the PAnDs and incorporated plasmonic nanoparticles (FIG. 10b). PAnDs were synthesized as described above, diluted and optical density was measured in a 1 cm plastic cuvette. Second, dynamic light scattering (DLS, DelsaNano C, Beckman Coulter) was used to determine the size distribution of the nanocarrier agent. PAnDs at synthesized concentration were measured and the resulting size distribution correlated with the pore size of the extruder filter used to size the PAnDs, 200 nm for these experiments. Finally, cryogenic transmission electron microscopy (cTEM, FEI Tecnai G2 F20) was used to image the PAnDs (FIG. 5). This method allows visualization of an intact PAnD and the metal nanoparticles within. As prepared PAnDs were diluted by 100 times and placed on holey carbon grids and vitrified in liquid ethane using a Vitrobot™ (FEI) with a 1.0 second blotting time. Samples were rapidly transferred to liquid nitrogen and stored until imaging. Nanoparticle encapsulation was verified by sample stage rotation to view the sample at 0, 45, and −45 degrees. These three forms of nanocarrier contrast agent characterization allowed for study of both physical and optical characteristics.

Contrast Mechanisms of Photoacoustic Nanodroplets.

PAnDs are a nano-sized agent consisting of a BSA shell and liquid PFC core, namely perfluoropentane with a boiling point of 27° C., in which specially capped plasmonic noble metal nanoparticles have been encapsulated (FIG. 1.) PAnDs are stable because while their nanoscale size increases surface tension, the BSA shell dramatically lowers the surface tension and prevents coalescence, thus preventing premature vaporization of super-heated PFC from both clinically relevant imaging ultrasound fields and elevated temperatures (up to 50° C. for 200 nm diameter droplets). Therefore, pulsed laser irradiation is used to activate this contrast agent, i.e., to remotely trigger the phase transition of PFC. The PAnDs are vaporized when encapsulated plasmonic nanoparticles, such as gold nanorods, absorb electromagnetic energy from the laser, providing localized heating well over the required vaporization temperature of PFC (steps 1 through 2 in FIG. 9). In addition, a high frequency pressure wave is generated at the surface of the plasmonic nanoparticles. Together, heat and pressure provide the conditions required to nucleate a liquid-to-gas phase transition of PFC, and the PAnD undergoes a vaporization which overcomes the surface tension of the BSA coating (step 3 in FIG. 9). The photoacoustic transient produced via vaporization is substantially larger than subsequent transients produced from the expelled plasmonic nanoparticles which undergo thermal expansion under continued pulsed laser irradiation (steps 4-5 in FIG. 9). Furthermore, the resulting gaseous phase also provides increased acoustic impedance mismatch between gas bubbles and the surrounding medium (step 6 in FIG. 9), providing, in essence, optically triggered ultrasonic contrast enhancement. Overall, PAnDs provide several types of contrast for two imaging modalities: vaporization and thermal expansion for photoacoustic imaging and gas-tissue acoustic impedance mismatch for ultrasound imaging.

Characterization of PAnDs.

After synthesis of PAnDs via an oil-in-water emulsion technique (see methods above), several approaches were used to characterize PAnDs. First, cryogenic transmission electron microscopy (cTEM) illustrates the spherical PFC droplets containing plasmonic gold nanorods with an overall size, controlled to approximately 200 nm using an extruding technique (FIG. 10a). cTEM imaging also confirms that the overall diameter and extent of nanoparticle loading can be controlled during the synthesis process. FIG. 10c displays a 200 nm PAnD purposefully without any nanoparticle loading, while FIG. 10d displays a 200 nm droplet designed to have a lesser extent of gold nanorod loading. FIG. 10e displays a PAnD sized to 400 nm with gold nanorod loading. Furthermore, different types of nanoparticles including iron-oxide particles, gold nanospheres, or silver nanoplates (FIG. 10f), and dyes can be incorporated into PAnDs. Second, spectrophotometry was used to ensure that the surface modification process did not alter the specifically tuned optical properties of the gold nanorods. The "as prepared" and "modified" gold nanorod spectra indicated only very small differences, and therefore the optical properties were not significantly altered during the ligand exchange process. Finally, dynamic light scattering (DLS) was used to confirm sizing diameters. It was found that the size distributions closely corresponded with the size of the extruder membranes used. For a particular imaging or therapeutic application, PAnDs can be customized allowing for adjustments of size, loading and surface functionalization.

Example 6

Photoacoustic and Ultrasound Imaging In Vitro

PAnDs were incorporated into a 10% polyacrylamide (Sigma Aldrich) hydrogel phantom crosslinked with a 0.1% w/v ammonium persulfate (Sigma Aldrich) in a 1:20 volume ratio of agent to polyacrylamide solution for a final concentration of $5.5 \times 10^6$ PAnDs/ml (optical image in FIG. 13b). The phantom was positioned in a water bath and imaged from the top using a 7 MHz, 1.4 cm aperture, 128 element, linear array transducer. A tunable laser system (optical parametric oscillator pumped by a Q-switched pulsed Nd:YAG laser, Opotek)

operating at 780 nm wavelength light, 5.0 mJ/cm² pulse energy, 10 Hz pulse repetition rate, and 5-7 ns pulse duration, was used to irradiate the phantom perpendicular to the imaging plane at 28 different locations for 60 seconds. Ultrasound radiofrequency signals were collected before and after each laser irradiation application. Photoacoustic radiofrequency signals were collected during laser irradiation. Ultrasound and photoacoustic images were reconstructed retrospectively from the captured data. Specifically, the radiofrequency ultrasound signals collected at each transducer were Hilbert transformed and beamformed, and then the amplitude of the signal was scan converted and displayed using either a linear (photoacoustic) or logarithmic (ultrasound) scale (20 dB). To form photoacoustic images displaying photoacoustic response from all 28 laser beam positions, photoacoustic images at each individual position were normalized and added to produce the final photoacoustic image.

Combined photoacoustic and ultrasound imaging demonstrates the contrast enhancement provided by PAnDs. Experiments were performed using a block-shaped hydrogel made out of an optically transparent, 10% polyacrylamide gel, homogenously laden with 200 nm PAnDs containing gold nanorods (see above methods for details). The hydrogel-based phantom was placed in a water tank and imaged before, during, and after laser irradiation using a 7 MHz ultrasound transducer array positioned at the top of the phantom. An optical beam generated from a tunable pulsed laser system (780 nm wavelength, 5-7 ns pulse duration, 10 Hz pulse repetition rate, 5.0 mJ/cm²) was focused sequentially onto the phantom at varying depths from 1 to 2 cm. Photoacoustic transients were collected at 3.3 Hz for 30 seconds. The initial photoacoustic signal corresponding to the vaporization of PAnDs was substantially higher than the subsequent transients corresponding to thermal expansion. When comparing the photoacoustic images (FIG. 11a) the vaporization signal had higher intensity than the thermal expansion. Furthermore, photoacoustic intensity measured over time (i.e., as the pulsed laser irradiation continues) presented a rapid decay of the signal magnitude (FIG. 11b) corresponding to the expected difference in the mechanisms of photoacoustic signal generation. The initial signal collected before laser irradiation illustrates the level of noise inherent in the imaging system. Once the laser was turned on, there was a dramatic increase in photoacoustic signal magnitude due primarily to the rapid, laser triggered vaporization of PAnDs. As laser irradiation continued, and the supply of PAnDs was depleted, the photoacoustic signal decayed to its steady-state level corresponding to the thermal expansion of the expelled gold nanorods. In biological tissue, unlike the case of the hydrogel phantom, thermal expansion from endogenous optical absorbers will also contribute to the photoacoustic signal.

Using the same phantom and experimental setup, several more locations (28 total) underwent pulsed laser irradiation in sequence where photoacoustic signals were captured for each laser pulse. These locations were strategically placed to "write" the letters "U" and "T." The reconstructed photoacoustic images of the phantom (FIG. 12a) confirm that under the same laser fluence, vaporization of PAnDs results in a stronger photoacoustic signal compared to nanorod-assisted photoacoustic signal generated by thermal expansion alone. The vaporization-based photoacoustic image displays a signal-to-noise ratio (SNR) of 7.3 dB, while the thermal expansion-based photoacoustic image displays a SNR of 1.3 dB. Furthermore, the average photoacoustic signal increase from all 28 positions is approximately 13 times, or 22 dB, higher than the thermal expansion signal, with a maximum reaching 66 times, or 37 dB, higher. Therefore, laser-induced vaporization of the PAnDs produced a significantly stronger photoacoustic signal than that of thermal expansion. We measured the photoacoustic signal generated by the vaporization of the PFC in PAnDs (first laser pulse, steps 2-3 in FIG. 9) and the thermal expansion of the nanorods that were expelled into the surrounding environment (subsequent laser pulses, repeated steps 5-6 in FIG. 9). The change in photoacoustic signal magnitude was significant (FIG. 11b)—vaporization of PAnDs resulted in a strong photoacoustic signal that was measurably higher compared to photoacoustic transients produced by thermal expansion. Importantly, the results of the phantom experiment also indicated that the same amplitude of the photoacoustic signal can be obtained with lower concentrations of gold nanorods inside of PAnDs compared to nanorods alone (FIG. 12b). Overall, vaporization of the PAnD contrast agent provided stronger photoacoustic signal as compared to the thermal expansion photoacoustic phenomena mediated by plasmonic nanoparticles.

Furthermore, once the vaporization of PAnDs was initiated, the generated gaseous phase of the PFC had a significant acoustic impedance mismatch with the surrounding environment, thus acting as an ultrasound contrast agent (FIG. 13). FIG. 13a shows how the resulting gaseous PFC will act to increase ultrasonic contrast by increased acoustic impedance mismatch in the phantom. The liquid-to-gas transition of PAnDs is illustrated in the optical images in FIG. 13b. The left panel of FIG. 13b contains light microscopy images of PAnDs suspended in a hydrogel block. The hydrogel was irradiated with a pulsed laser beam and additional optical images were taken (right panel in FIG. 13b). The large size of gas bubbles appearing in FIG. 13b were due to coalescence of several individual microbubbles in close proximity. During the photoacoustic imaging experiment (FIG. 12a), ultrasound signals were collected before and after each laser application. With point-by-point optical laser activation of PAnDs, the ultrasound contrast appears at the corresponding positions of the laser-PAnD interaction (FIG. 13c) due to an ultrasound pulse backscattered from PAnD generated microbubbles. Therefore, vaporization of the PFC in PAnDs also provides increased ultrasound contrast.

Example 7

Concentration Vs. Photoacoustic Signal Amplitude Study

To determine the photoacoustic signal produced from varying concentrations of PAnDs as compared to the equivalent concentration of gold nanorods, experiments were conducted using 40 nm by 10 nm nanorods and PAnDs incorporating the same nanorods. The results of this study are displayed in FIG. 12c. A thin, 0.2 mm diameter, glass tube was suspended in a water cuvette, and known concentrations of either PAnDs (containing of 0.25, 0.125, and 0.0625 fraction of the original, as-prepared concentration of nanorods) or nanorods alone (1.0, 0.5, and 0.25 of the original concentration) were injected into the sample tube. A pulsed (10 Hz, 5-7 ns pulse duration) laser beam was use to irradiate the sample with 780 nm light at 5 mJ/cm² from the side. Photoacoustic signal was collected using a 7.5 MHz, single element ultrasound transducer positioned above the sample in the water tank. Peak signal was averaged for three samples per condition, and plotted using error bars representing one standard deviation.

Example 8

Cytotoxicity Study

PAnDs, prepared as previously described ($10^8$ PAnDs/ml), were used for this study. PAnDs (5 ml) were sterilized under UV light for 20 min. The sterilized PAnDs were then centrifuged and resuspended in sterile cell media at overall concentrations of up to 1.2 mg/ml. A 96 well plate was seeded with 10,000 MPanc96 pancreatic cancer cells per well and incubated at 37° C. and 5% $CO_2$ for 24 hours prior to further incubation with PAnDs. The media (DMEM with 10% FBS and 1% pen-strep) was aspirated, and the new media containing varying concentrations of PAnDs was placed in the predetermined wells. The plate was incubated for another 24 hours at 37° C. and 5% $CO_2$. An initial absorbance was measured using a plate reader (BioTek, Synergy HT) at 490 nm Next, 20 μl of 3-(4,5-dimethylthiazol-2-yl)-5-(3-carboxymethoxyphenyl)-2-(4-sulfophenyl)-2H-tetrazolium (MTS) was added to each well and incubated at 37° C. and 5% $CO_2$ for 2 hours. The mitochondrial activity in viable cells reduces the MTS to a formazan product that has a peak optical absorbance at 490 nm. A final absorbance reading was taken. The initial absorbance reading of each well was subtracted from the final reading to determine the relative viability values. A one way ANOVA was used to determine statistically significant different mean viabilities between the control wells and the wells incubated with varying concentrations of PAnDs. With a resulting p-value of 0.8756 for the highest concentration of 1.2 mg/ml PAnDs, the null hypothesis that the absorbance means are the same cannot be rejected. Therefore, since the absorbance means between control wells and wells with PAnDs were not statistically significantly different, the PAnDs exhibited no cytotoxicity on the cells as determined by this MTS assay.

Example 9

Photoacoustic and Ultrasound Imaging In Vivo

PAnDs were synthesized as previously described at a concentration of $10^8$ PAnDs/ml with approximately 10 gold nanorods per droplet as determined by spectrophotometry and cTEM, and then sized to 400 nm using a lipid miniextruder. A female, 3 month old, nu/nu mouse (Charles River Laboratory) was anesthetized using 1.5% isoflurane and 2.5% oxygen following proper animal care and use protocols. The spleen and pancreas were located using a Vevo2100 ultrasound imaging system (VisualSonics) equipped with a 40 MHz, 256 element array transducer. To generate photoacoustic transients, the tissue was irradiated with a laser beam (780 nm wavelength, 5-7 ns pulses, 10 Hz pulse repetition frequency, 14 mJ/cm² fluence) generated by a Nd:YAG Q-switched pulsed laser pumping an optical parametric oscillator (Newport—Spectra Physics). Control ultrasound and photoacoustic images were taken before nanoparticle injection. Using a needle, 100 μl of an equal volume mixture of PAnDs and Matrigel (BD Biosciences), used to prevent high levels of migration of the PAnDs away from the injection site, were injected into the pancreas of the mouse under ultrasound image guidance. Matrigel has peak absorption at approximately 461 nm, and, as confirmed in previous experiments, does not produce appreciable photoacoustic signal in response to 780 nm laser irradiation. After the injection, photoacoustic signals were recorded prior and during pulsed laser irradiation (475 laser pulses). The ultrasound and photoacoustic images were reconstructed off-line and displayed using a linear (photoacoustic) or logarithmic (ultrasound) scale.

While PAnDs produced high levels of contrast enhancement in in vitro phantoms studies, it is important to test their performance in an in vivo setting. A murine model was adapted for in vivo studies. Under ultrasound guidance, an anesthetized nu/nu mouse was injected with 50 μl of PAnDs at a concentration of $10^8$ PAnDs/ml into the pancreas, which resides under the spleen at approximately 5 to 7 mm of depth from the skin surface. The spleen represents a highly optically absorbing organ due to its high blood content. Imaging through the blood-laden spleen and at depth in the pancreas represents a challenge for PA imaging applications, and therefore it was chosen as an imaging target to exhibit the contrast enhancing capabilities of PAnDs. Using a Vevo2100 (VisualSonics, Inc.) ultrasound imaging system equipped with a 40 MHz, 256 element transducer, ultrasound pulse-echo signals and photoacoustic transients where collected. Photoacoustic transients were generated under pulsed laser irradiation (10 Hz, 5-7 ns pulse duration, 14 mJ/cm²) using a tunable laser system operating at 780 nm (the peak optical absorption of the gold nanorods encapsulated within PAnDs). For more details, please see methods section.

Photoacoustic images were collected for 475 laser pulses (i.e., 475 photoacoustic frames). Initially, the laser beam was blocked from irradiating the animal to prevent unrecorded vaporization of PAnDs and to determine the noise level of the imaging system. Upon radiation, the photoacoustic signal within the region of interest corresponding to injected PAnDs was initially very strong and, as the pulsed laser irradiation continued, it decayed to the level corresponding to superposition of signals from the expelled nanorods and endogenous thermal expansion (FIG. 14a). The vaporization signal was 4.3 dB higher than that given by the nanorod and endogenous chromophores combined. Based on control experiments (described in methods above), using the equivalent number of nanorods as encapsulated in the injected PAnDs, the increase of signal generated by the nanorods alone was approximately 1.9 dB, for a total of 6.0 dB increase in signal generation using PAnDs. The corresponding combined photoacoustic and ultrasound images in FIG. 14b and FIG. 14c illustrate the peak photoacoustic signals corresponding to vaporization of PAnDs and thermal expansion. As evident from FIG. 14, the photoacoustic signal produced by the initial vaporization is much stronger than the signal produced by thermal expansion.

PAnDs Versus Gold Nanorod Efficiency.

An in vivo experiment was undertaken to determine how effective PAnDs are in producing photoacoustic contrast as compared to the traditional contrast agent, plasmonic gold nanorods alone. To define the exact amount of nanorods encapsulated in the injected amount of PAnDs in the in vivo experiment, several samples were analyzed using spectrophotometry. The spectrum of highly scattering and absorbing PAnDs loaded with gold nanorods was compared with the optically scattering spectra of empty PAnDs to estimate the absorption of nanorods encapsulated in PAnDs. A solution of nanorods with polyethylene glycol grafted to their surface was diluted in water until the optical density matched that of the encapsulated nanorods. Using an anesthetized Nu/Nu mouse and the same imaging setup used in the in vivo experiment above, baseline photoacoustic and ultrasound images were taken to evaluate the endogenous contrast inherent in a mouse spleen and pancreas. The noise floor of photoacoustic imaging system was evaluated using these images. Then, 50 μl of the diluted nanorod solution, for a total of approximately $5 \times 10^8$ nanorods, was injected using the same protocol as the in vivo experiment.

The animal was imaged and changes in photoacoustic intensity during continued laser irradiation were analyzed, as displayed in FIG. 14 d-f. A comparison of photoacoustic signal from thermal expansion caused by endogenous photoabsorbers and the photoacoustic signal from thermal expansion caused by both the endogenous photoabsorbers and the injected gold nanorods revealed that the associated signal increase is 24%, or 1.9 dB. The percentage difference in signal provided by an absolute number of nanorods can be used to determine the overall photoacoustic signal enhancement caused by PAnDs above the endogenous contrast of the animal with the same absolute number of nanorods encapsulated. Furthermore, it is pertinent to note that under the laser fluence used in our experiments, the gold nanorods remained thermodynamically stable and, therefore, do not exhibit photoacoustic signal change with laser irradiation. Furthermore, nanorods alone do not induce vaporization comparable to PAnDs. The photoacoustic and ultrasound signals as the laser irradiated the sample at the first/last photoacoustic frames collected are depicted in FIG. 14 e-f. As expected, there was no change in these images with continuing laser irradiation.

PAnDs not only produce significant enhancement of photoacoustic contrast in a mouse model; PAnDs also provide significant ultrasound contrast once injected and remotely triggered. Ultrasound images of a mouse cross-section before injection of PAnDs and after the laser activation injected PAnDs are shown in FIG. 15. Due to the dynamic respiratory/cardiac motion and the nature of internal organs, ultrasound contrast varies due to migration of PAnDs and bubbles in and out of the imaging plane, coalescence of bubbles, gas diffusion, and delayed vaporization of PAnDs. The peak increase of ultrasound contrast was 3.1 dB over post injection images, and approximately 29 dB over native ultrasound images. This experiment demonstrates optically triggered, ultrasound contrast enhancement in a living, biological system.

Based on the preceding examples, the developed contrast agent, namely photoacoustic nanodroplets, can be remotely triggered to provide both ultrasound and photoacoustic contrast enhancement through vaporization and gas bubble formation. As such, the PAnDs are naturally applicable for combined photoacoustic and ultrasound imaging. Overall, PAnDs provide three mechanisms of contrast enhancement: a one-time, laser-induced vaporization of the PFC within PAnDs to produce photoacoustic contrast; long term thermal expansion induced by the plasmonic nanoparticles absorbing laser energy and yielding photoacoustic contrast; and acoustic impedance mismatch between the surrounding tissues and the microbubbles containing PFC in gaseous phase producing ultrasound contrast. These three contrast mechanisms have been demonstrated to produce high levels of contrast enhancement both in phantom and live animal experiments, confirming the feasibility of the PAnDs as an optically triggered, dual contrast agent for clinical photoacoustic and ultrasound imaging. These contrast mechanisms were not only demonstrated in a hydrogel phantom, but also in a biological environment to show efficacy in tissues. Compared to phantoms, tissue experiments are associated with several challenges including increased optical absorption and scattering, a high level of background photoacoustic signal due to endogenous chromophores, such as melanin and hemoglobin, and higher laser fluence required to image at sufficient depth. The in vivo studies were critical to demonstrate the applicability of PAnDs to overcome challenges provided by imaging in a biological setting. Furthermore, these studies suggest that use of PAnDs for photoacoustic imaging in clinical applications is feasible.

Beyond inducing large photoacoustic transients, the gaseous phase of the PFC serves a secondary function as a remotely triggered ultrasound contrast agent. Indeed, the PAnDs have high surface tension that prevents them from vaporizing under clinically relevant ultrasound fields and slight variations of temperatures. Conversely, micro-sized PFC droplets do not experience the same surface tension, burst easily, but have a limited ability to enter interstitial space due to their larger size compared to PAnDs. Therefore, until exposure to laser irradiation and optical absorption of the laser energy by the plasmonic nanoparticles occurs, the PAnDs remain inert and virtually undetectable by conventional ultrasound imaging. The ultrasound images in FIG. 13c are shown in a non-scattering background and therefore the US signals are easy to visualize. In a scattering media such as tissue, as depicted by the in vivo mouse study, the contrast is not as dramatic. However, various acoustic techniques such as nonlinear or second harmonic acoustic spectroscopy may be implemented to further enhance the contrast. Therefore, the PAnD-based platform provides a nano-scale, biocompatible (see methods above for details), and efficient contrast agent for both photoacoustic and ultrasound imaging. In addition, the developed platform can utilize broad spectrum of electromagnetic wave "triggers" by incorporating the corresponding thermally responsive particles within the PFC droplets.

PAnDs have several benefits for biological imaging due to their unique physical properties. As vaporization provides stronger photoacoustic signal than thermal expansion, by employing PAnDs, a smaller number of noble metal nanoparticles can be used in biological and clinical applications of photoacoustic imaging, reducing the potential toxic effects of plasmonic particles[41]. Furthermore, in biological tissues increased fluence is required to image at sufficient depth. At fluences as low as 8 mJ/cm$^2$, gold nanorods can become thermodynamically unstable and this can significantly change their optical properties. PAnDs produce higher photoacoustic signal with only limited laser exposure, as indicated in our phantom and mouse imaging, effectively rendering the thermal stability of nanorods of limited concern. This increased signal can even aid in providing photoacoustic imaging at depths beyond what is obtainable using traditional plasmonic contrast agents and dyes. Finally, regardless of the initial surface fluence of the light delivery, within several centimeters of depth in tissue, the fluence has greatly decreased. As exhibited by phantom experiments, PAnDs require only minimal energy (a fluence of a few mJ/cm$^2$) to activate into their contrast enhancing state, making them able to provide contrast deep within tissues. Recent studies have revealed that photoacoustic imaging at alternative wavelengths, specifically 1064 nm, minimizes endogenous contrast of the tissues, enabling increased imaging depth. Furthermore, the ANSI laser exposure standard also dramatically increases to approximately 100 mJ/cm$^2$ in this infrared region. PAnDs can be easily tuned to vaporize at a desired wavelength by changing the aspect ratio of the nanorod, or encapsulating a different plasmonic particle that has peak absorption at the desired wavelength. Therefore, PAnDs are designed to be used in biological contrast enhancing applications.

Beyond its use as a dual contrast agent, PAnDs are adaptable for a variety of applications ranging from fundamental biomedical studies to medical diagnostic and therapeutic applications. First, they can be loaded with organic chemotherapeutics that would be selectively released at the location of laser activation. In order to use chemotherapeutics properly, an initial injection of contrast agent without the drug may be used to image (i.e., locate and diagnose) the pathology, and then a second, drug-loaded injection could be used to safely introduce a therapeutic agent. Furthermore, the surface of the PAnD can be modified to allow for molecular targeting of specific biological targets (FIG. 1). Finally, a plethora of other therapeutic effects could be optimized using PAnDs, including targeted image-guided photothermal therapy, drug delivery and release, vessel occlusion, and cell membrane sonoporation effects from vaporization.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

REFERENCES

The following references, to the extent that they provide exemplary procedural or other details supplementary to those set forth herein, are specifically incorporated herein by reference.

Byrne et al., "Active targeting schemes for nanoparticle systems in cancer therapeutics," *Adv Drug Deliv Rev*, vol. 60, pp. 1615-26, Dec. 14, 2008.
Drezek et al., *Small*, 4, No. 1, 26-49, 2008.
Korpanty et al., *Ultrasound in Med. & Biol., Vol.* 31, No. 9, pp. 1279-1283, 2005.
Kumar et al., *Nature Protocols*, Vol. 3, No. 2, pp. 314-320, 2008.
Wilson, K., Homan, K. & Emelianov, S. Biomedical photoacoustics beyond thermal expansion using triggered nanodroplet vaporization for contrast-enhanced imaging. Nature Communications 3, 618 (2012).
Nikoobakht, B. & El-Sayed, M. A. Preparation and Growth Mechanism of Gold Nanorods (NRs) Using Seed-Mediated Growth Method. *Chemistry of Materials* 15, 1957-1962 (2003).
Thierry, B., Ng, J., Krieg, T. & Griesser, H. J. A robust procedure for the functionalization of gold nanorods and noble metal nanoparticles. *Chem Commun (Camb)*, 1724-1726 (2009).
Zou, X., Ying, E., Chen, H. & Dong, S. An approach for synthesizing nanometer-to micrometer-sized silver nanoplates. *Colloids and Surfaces A: Physicochemical and Engineering Aspects* 303, 226-234 (2007).
Ledwith, D. M., Aine M. Whelan and John M. Kelly A rapid, straight-forward method for controlling the morphology of stable silver nanoparticles. *Journal of Material Chemistry* 17, 2459-2464 (2007).

What is claimed is:

1. A method of imaging comprising:
   providing a nanocarrier contrast agent composition comprising:
      an organic liquid comprising a plurality of nanoparticles dispersed therein, and
      a coating material disposed around the exterior surface of the organic liquid;
      applying energy to a biological tissue comprising the nanocarrier composition, wherein applying energy to the biological tissue results in at least partial vaporization of the organic liquid; and
   imaging a biological tissue comprising the nanocarrier contrast agent composition.

2. The method of claim 1, wherein applying energy to the biological tissue comprises irradiating at least a portion of the biological tissue with a light source or applying a radio frequency field.

3. The method of claim 1, wherein the nanocarrier contrast agent further comprises a therapeutic agent.

4. The method of claim 3, wherein applying energy to the biological tissue results in release of the therapeutic agent from the nanocarrier composition.

5. The method of claim 1, wherein imaging the biological tissue comprises application of at least one imaging technique selected from the group consisting of: photoacoustic imaging, ultrasound imaging, optical imaging, magnetic resonance imaging, computed tomography, thermal imaging, nuclear imaging, magnetomotive imaging enhancement, and a combination thereof.

6. A method of therapy comprising:
   contacting a biological tissue with a nanocarrier contrast agent composition comprising:
      an organic liquid comprising a plurality of nanoparticles dispersed therein,
      a coating material disposed around the exterior surface of the organic liquid, and
      a therapeutic agent; and
   applying energy to the biological tissue, wherein applying energy to the biological tissue results in at least partial vaporization of the organic liquid.

7. The method of claim 6, wherein applying energy to the biological tissue results in release of the therapeutic agent from the nanocarrier contrast agent composition.

8. The method of claim 7, wherein applying energy to the biological tissue comprises irradiating at least a portion of the biological tissue with a light source or applying a radio frequency field.

9. The method of claim 6, wherein the therapeutic agent is in the organic liquid.

10. The method of claim 6, wherein the therapeutic agent is on the exterior surface of the nanocarrier composition.

11. The method of claim 6, wherein the nanocarrier contrast agent further comprises a targeting moiety.

12. The method of claim 11, further comprising:
   allowing the nanocarrier contrast agent to accumulate in a region of the biological tissue, wherein the targeting moiety facilitated accumulation of the nanocarrier in the region.

13. The method of claim 11, wherein the targeting moiety comprises at least one targeting moiety selected from the group consisting of: an antibody, an antibody fragment, a peptide sequence, aptamer, folate, a ligand, a gene component, and a combination thereof.

* * * * *